(12) United States Patent
LaMarca et al.

(10) Patent No.: US 12,239,551 B2
(45) Date of Patent: Mar. 4, 2025

(54) SAGITTAL BALANCE SYSTEMS AND METHODS OF USE THEREOF

(71) Applicant: K2M, Inc., Leesburg, VA (US)

(72) Inventors: Frank LaMarca, Ann Arbor, MI (US); Robert Lee, Hertfordshire (GB); Gregory Poulter, Indianapolis, IN (US); Steven Tresser, Tampa, FL (US); Michael Wang, North Miami, FL (US); Josh Rubin, Reston, VA (US); Hadley Sis, Reston, VA (US); Nick Padovani, Fairfax, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 18/139,110

(22) Filed: Apr. 25, 2023

(65) Prior Publication Data
US 2023/0255793 A1    Aug. 17, 2023

Related U.S. Application Data

(63) Continuation of application No. 17/237,549, filed on Apr. 22, 2021, now Pat. No. 11,679,004, which is a
(Continued)

(51) Int. Cl.
*A61F 2/46* (2006.01)
*A61B 17/02* (2006.01)
(Continued)

(52) U.S. Cl.
CPC .......... *A61F 2/4611* (2013.01); *A61B 17/025* (2013.01); *A61F 2/30749* (2013.01);
(Continued)

(58) Field of Classification Search
CPC ... A61B 17/02; A61B 17/025; A61B 17/1757; A61F 2/30749; A61F 2/30771;
(Continued)

(56) References Cited

U.S. PATENT DOCUMENTS 6,159,244 A * 12/2000 Suddaby ............... A61F 2/4611
606/247
6,491,724 B1 * 12/2002 Ferree ..................... A61F 2/447
623/17.11
(Continued)

FOREIGN PATENT DOCUMENTS

JP       2018175851 A  * 11/2018 ............... A61F 2/44
WO   WO-2016183382 A1 * 11/2016 ........... A61F 2/4455

OTHER PUBLICATIONS

Extended European Search Report for Application No. 19202058.4 dated Mar. 6, 2020, 3 pages.

*Primary Examiner* — Eric S Gibson
(74) *Attorney, Agent, or Firm* — Lerner David LLP

(57) ABSTRACT

A system for dilating tissue includes a retractor having a pair of retractor blades that are movable towards and away from each other to retract tissue of a patient. The retractor blades have longitudinal guide channels. A first pin is attachable to a first vertebra. The system also includes an interbody spacer insertion device that has a guide channel for slidably engaging the longitudinal channel guide and is releasably attachable to an interbody spacer. The interbody spacer insertion device is configured to guide the interbody spacer into a space between adjacent vertebrae. A method for using the system includes advancing the retractor blades towards first and second vertebrae. The first retractor blade is attached to the first vertebra using the first pin and the retractor blades are moved away from each other. The interbody spacer insertion device is translated towards the vertebrae to position the interbody spacer between the vertebrae.

20 Claims, 20 Drawing Sheets

Related U.S. Application Data continuation of application No. 16/156,600, filed on Oct. 10, 2018, now Pat. No. 11,013,616.

(51) Int. Cl.
   *A61F 2/30* (2006.01)
   *A61F 2/44* (2006.01)

(52) U.S. Cl.
   CPC ........ *A61F 2/30771* (2013.01); *A61F 2/4425* (2013.01); *A61B 2017/0256* (2013.01); *A61F 2002/30405* (2013.01); *A61F 2002/30784* (2013.01); *A61F 2002/30934* (2013.01); *A61F 2/4603* (2013.01); *A61F 2002/4615* (2013.01); *A61F 2002/469* (2013.01)

(58) Field of Classification Search
   CPC .......... A61F 2/44; A61F 2/442; A61F 2/4425; A61F 2/4455; A61F 2/446; A61F 2/4465; A61F 2/447; A61F 2/46; A61F 2/4603–4611; A61F 2002/4615; A61F 2002/4627
   See application file for complete search history.

(56) References Cited

U.S. PATENT DOCUMENTS

| | | | | |
|---|---|---|---|---|
| 6,562,074 | B2* | 5/2003 | Gerbec | A61F 2/4611 |
| | | | | 623/17.15 |
| 7,044,971 | B2* | 5/2006 | Suddaby | A61F 2/4455 |
| | | | | 623/17.11 |
| 7,235,105 | B2* | 6/2007 | Jackson | A61F 2/4611 |
| | | | | 623/17.16 |
| 7,678,148 | B2* | 3/2010 | Peterman | A61F 2/4455 |
| | | | | 623/17.11 |
| 8,303,658 | B2* | 11/2012 | Peterman | A61F 2/447 |
| | | | | 623/17.11 |
| 8,425,576 | B2* | 4/2013 | Anderson | A61B 17/8052 |
| | | | | 606/294 |
| 8,827,902 | B2* | 9/2014 | Dietze, Jr. | A61B 17/0293 |
| | | | | 600/231 |
| 8,852,089 | B2* | 10/2014 | Blackwell | A61B 17/0206 |
| | | | | 600/210 |
| 8,864,770 | B2* | 10/2014 | Blain | A61F 2/4455 |
| | | | | 606/86 A |
| 8,945,227 | B2* | 2/2015 | Kirschman | A61B 17/70 |
| | | | | 623/17.16 |
| 9,393,130 | B2* | 7/2016 | Suddaby | A61F 2/4611 |
| 9,427,330 | B2* | 8/2016 | Petersheim | A61B 17/809 |
| 9,566,163 | B2* | 2/2017 | Suddaby | A61F 2/4425 |
| 9,808,353 | B2* | 11/2017 | Suddaby | A61F 2/46 |
| 10,045,797 | B1* | 8/2018 | Walkenhorst | A61F 2/447 |
| 10,080,666 | B2* | 9/2018 | Suddaby | A61F 2/4425 |
| 10,137,006 | B2* | 11/2018 | Dewey | A61F 2/447 |
| 10,137,007 | B2* | 11/2018 | Dewey | A61F 2/4455 |
| 10,610,375 | B2* | 4/2020 | Quinlan | A61F 2/447 |
| 10,973,653 | B2* | 4/2021 | Iott | A61F 2/447 |
| 11,013,616 | B2* | 5/2021 | LaMarca | A61F 2/4611 |
| 11,058,552 | B2* | 7/2021 | Zink | A61B 90/90 |
| 11,291,558 | B2* | 4/2022 | Laine | A61F 2/447 |
| 11,679,004 | B2* | 6/2023 | LaMarca | A61B 17/1757 |
| | | | | 623/17.16 |
| 2002/0128713 | A1* | 9/2002 | Ferree | A61F 2/4465 |
| | | | | 623/17.11 |
| 2004/0044411 | A1* | 3/2004 | Suddaby | A61F 2/4455 |
| | | | | 623/17.15 |
| 2004/0193269 | A1* | 9/2004 | Fraser | A61B 17/7059 |
| | | | | 623/17.11 |
| 2005/0085913 | A1* | 4/2005 | Fraser | A61F 2/4455 |
| | | | | 606/279 |
| 2006/0030943 | A1* | 2/2006 | Peterman | A61F 2/447 |
| | | | | 623/17.11 |
| 2006/0217807 | A1 | 9/2006 | Peterman et al. | |
| 2008/0161925 | A1* | 7/2008 | Brittan | A61F 2/4611 |
| | | | | 623/17.16 |
| 2008/0294262 | A1* | 11/2008 | Levieux | A61F 2/4611 |
| | | | | 606/280 |
| 2008/0300634 | A1* | 12/2008 | Gray | A61F 2/4455 |
| | | | | 606/264 |
| 2009/0005784 | A1* | 1/2009 | Blain | A61B 17/025 |
| | | | | 606/86 A |
| 2009/0012529 | A1* | 1/2009 | Blain | A61B 17/808 |
| | | | | 606/86 A |
| 2009/0036746 | A1* | 2/2009 | Blackwell | A61B 17/0206 |
| | | | | 600/219 |
| 2009/0234362 | A1* | 9/2009 | Blain | A61F 2/4455 |
| | | | | 606/90 |
| 2009/0326580 | A1* | 12/2009 | Anderson | A61B 17/8047 |
| | | | | 606/301 |
| 2010/0121453 | A1* | 5/2010 | Peterman | A61F 2/4455 |
| | | | | 623/17.11 |
| 2010/0268339 | A1* | 10/2010 | Malinin | A61F 2/447 |
| | | | | 623/17.11 |
| 2012/0041272 | A1* | 2/2012 | Dietze, Jr. | A61B 17/025 |
| | | | | 600/231 |
| 2012/0088979 | A1* | 4/2012 | Nunley | A61B 17/0206 |
| | | | | 600/231 |
| 2012/0151736 | A1 | 6/2012 | Baudouin et al. | |
| 2014/0343678 | A1* | 11/2014 | Suddaby | A61F 2/4611 |
| | | | | 623/17.16 |
| 2015/0057755 | A1* | 2/2015 | Suddaby | A61F 2/4455 |
| | | | | 623/17.16 |
| 2015/0150689 | A1* | 6/2015 | Wang | C22C 1/0458 |
| | | | | 419/2 |
| 2015/0209152 | A1* | 7/2015 | Patterson | A61F 2/4455 |
| | | | | 623/17.13 |
| 2015/0289993 | A1 | 10/2015 | Jiang | |
| 2016/0287403 | A1* | 10/2016 | Suddaby | A61F 2/4425 |
| 2016/0331549 | A1* | 11/2016 | Petersheim | A61B 17/92 |
| 2017/0216045 | A1* | 8/2017 | Dewey | A61F 2/447 |
| 2017/0319352 | A1* | 11/2017 | Dewey | A61F 2/447 |
| 2018/0085105 | A1* | 3/2018 | Kim | A61B 17/0206 |
| 2018/0221155 | A1* | 8/2018 | Iott | A61B 17/8042 |
| 2018/0368992 | A1* | 12/2018 | Zink | A61F 2/4465 |
| 2019/0083279 | A1* | 3/2019 | Suddaby | A61F 2/447 |
| 2019/0091033 | A1* | 3/2019 | Dewey | A61F 2/4611 |
| 2019/0091034 | A1* | 3/2019 | Dewey | A61F 2/4611 |
| 2019/0110900 | A1* | 4/2019 | Suddaby | A61F 2/4455 |
| 2019/0133778 | A1* | 5/2019 | Johnston | A61F 2/30749 |
| 2019/0254840 | A1* | 8/2019 | Gray | A61F 2/447 |
| 2020/0113713 | A1* | 4/2020 | LaMarca | A61F 2/30749 |
| 2021/0236301 | A1* | 8/2021 | LaMarca | A61B 17/1757 |
| 2023/0255793 | A1* | 8/2023 | LaMarca | A61F 2/4611 |
| | | | | 623/17.16 |

\* cited by examiner

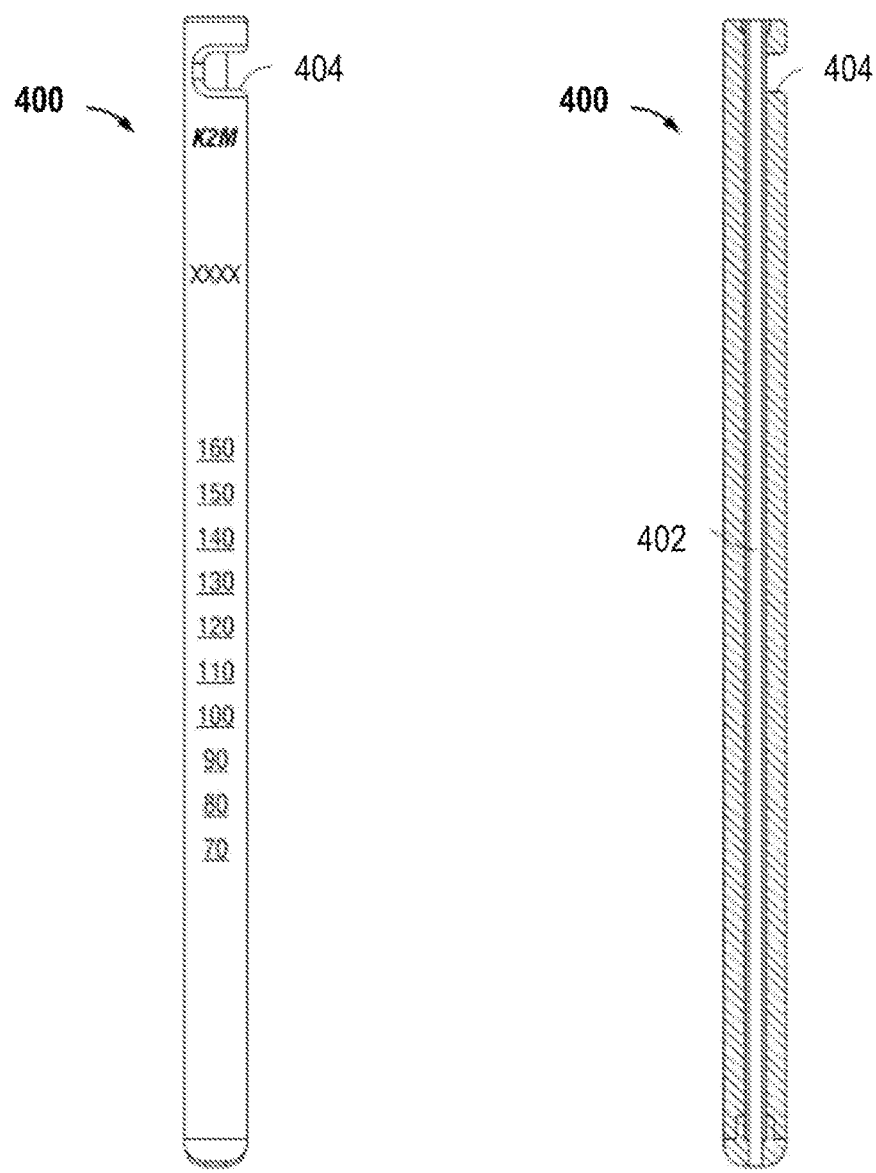

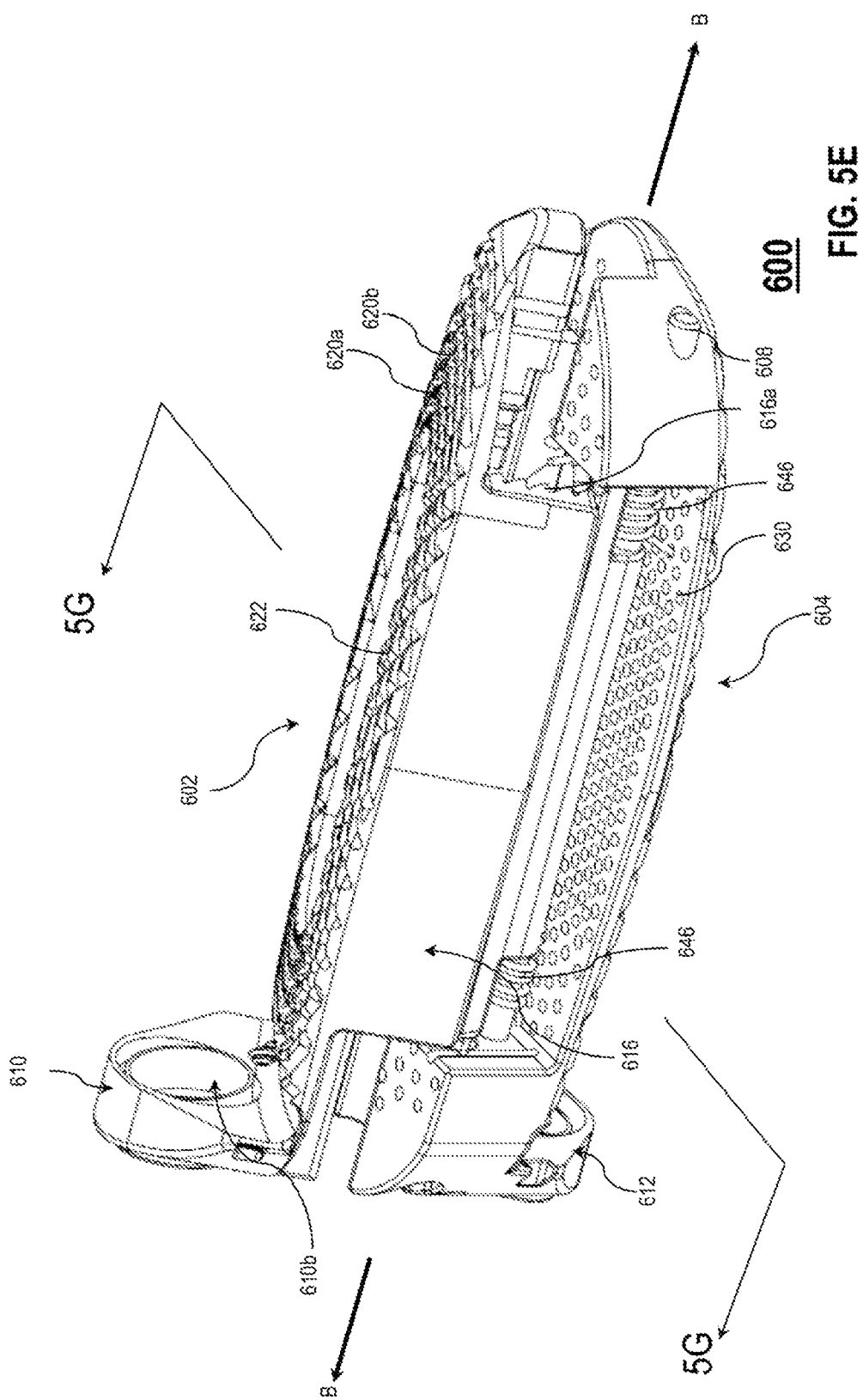

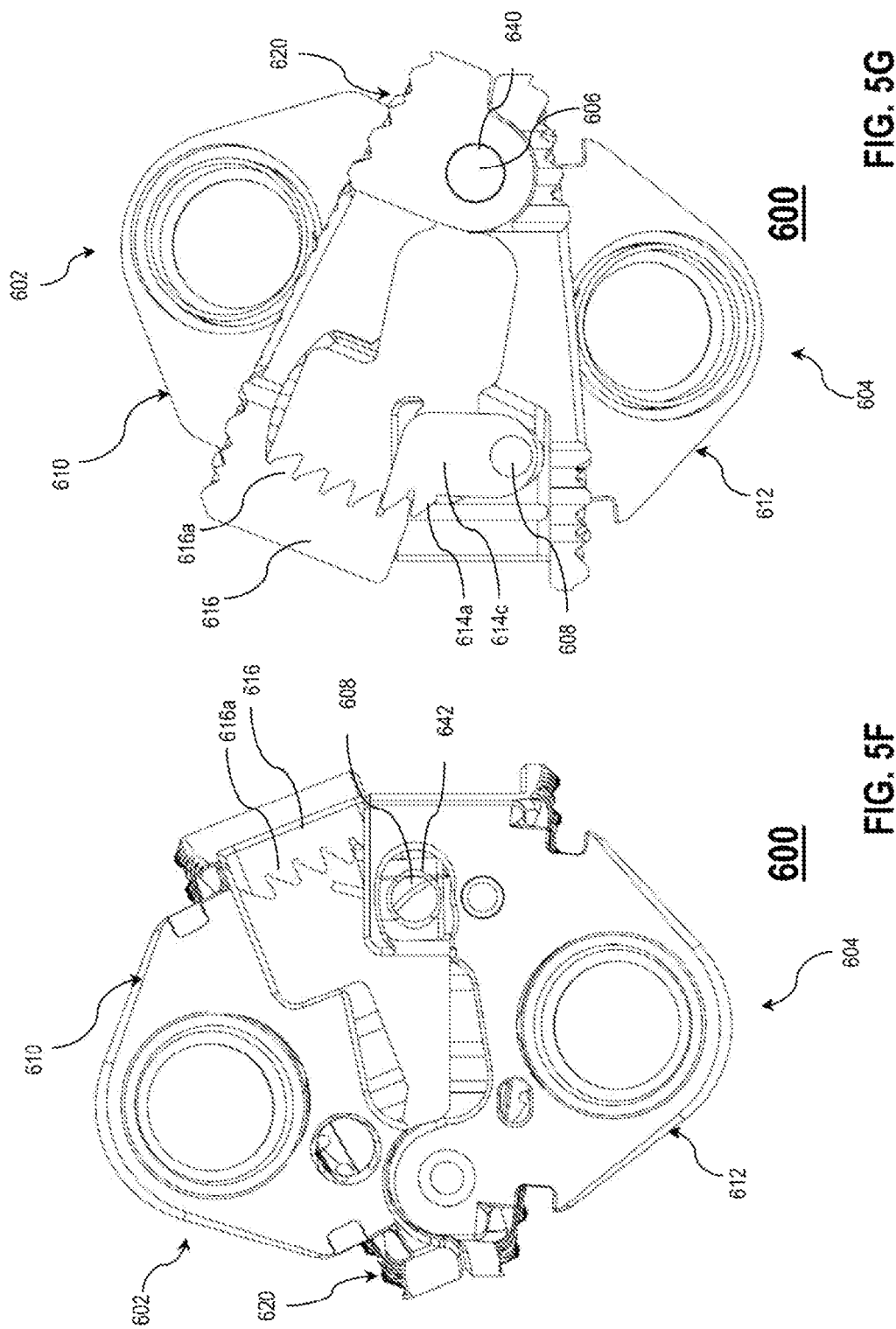

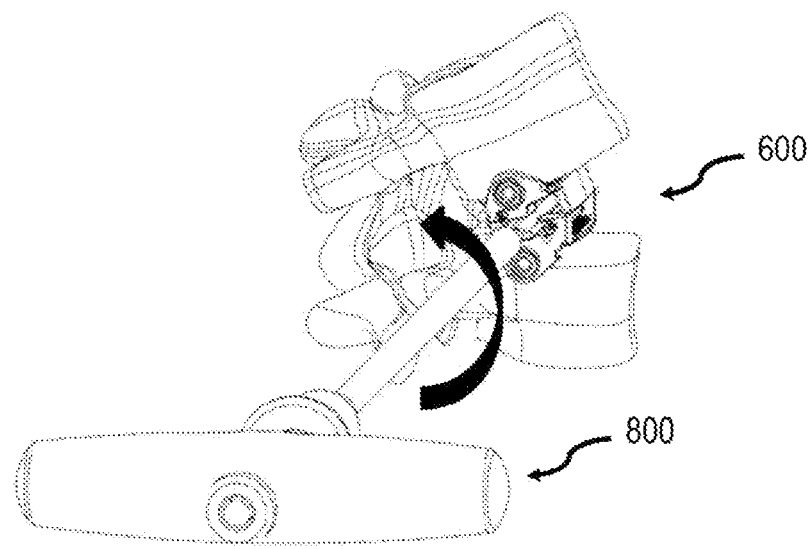
FIG. 8B
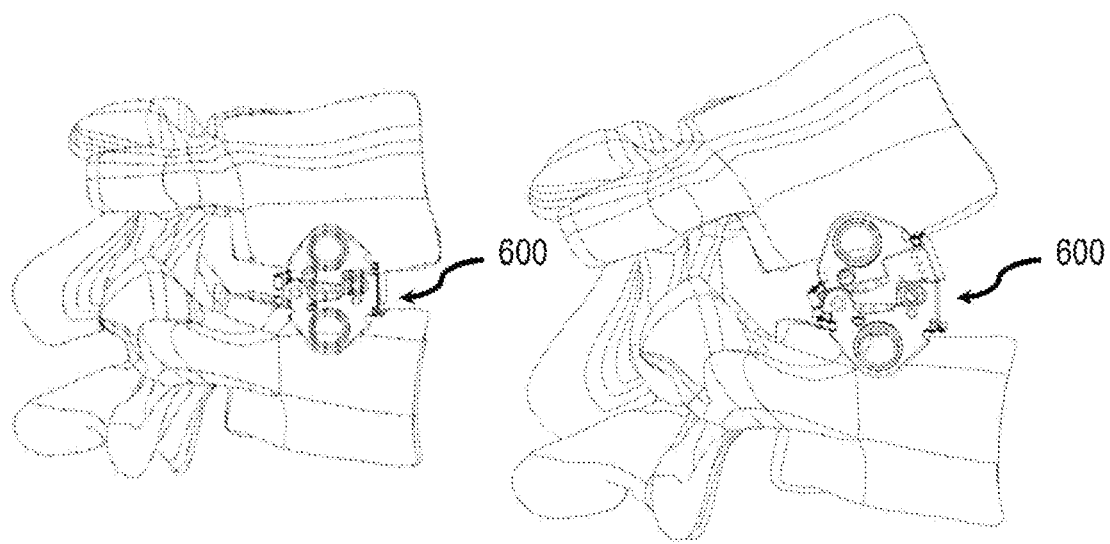
FIG. 8C
FIG. 8D

SAGITTAL BALANCE SYSTEMS AND METHODS OF USE THEREOF

CROSS REFERENCE TO RELATED APPLICATIONS

This application is a continuation of U.S. application Ser. No. 17/237,549, filed on Apr. 22, 2021, which is a continuation of U.S. application Ser. No. 16/156,600, filed on Oct. 10, 2018, now U.S. Pat. No. 11,013,616, the disclosures of which are incorporated herein by reference.

BACKGROUND

Technical Field

The present disclosure relates generally to systems and methods for performing lumbar surgical procedures.

Related Art

The human spine includes twenty-four vertebrae coupled sequentially to one another to form a spinal column that houses and protects critical elements of the nervous system. Each vertebra has a cylindrical body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs that provide flexibility to the spine and absorb shock during physical activity.

A small opening (i.e., a foramen) located between each vertebra allows for passage of nerves through the vertebrae. However, when the vertebrae are not properly aligned (e.g., are offset or constricted), the nerves may be compressed, leading to neurological disorders such as back pain, leg pain, numbness, tingling, diminished strength, a decrease in a range of motion of an individual, etc. Additionally, over time the intervertebral discs can deteriorate, tear, or herniate (where inner portions of the disc protrude through a tear), leading to constriction and/or misalignment of the discs and vertebrae, again causing chronic pain, degenerative disc disease, or even tearing or herniation.

Surgical procedures were developed to correct these issues, including procedures that remove and replace damaged intervertebral discs with prosthetics. Initially, during these procedures, access to a compromised disc and the corresponding vertebrae is achieved by creating an incision in a patient, guiding a retractor along a pathway to the target surgical site, and engaging the retractor to separate tissue between the initial incision and the target surgical site. After a partial or complete removal of the damaged disc (commonly referred to as a discectomy), the resulting empty space between the corresponding vertebrae may collapse and/or become misaligned due to the partial or complete absence of the disc. To prevent such collapse or misalignment clinicians may insert a prosthetic spacer between the vertebrae to maintain normal spacing and curvature of the affected region. Once the prosthetic is secured, the retractor is removed, and the initial incision closed.

Accordingly, improved systems and methods for performing surgical procedures to replace damaged intervertebral discs are desirable.

SUMMARY

According to aspects of the present disclosure, a method for performing a surgical procedure may include advancing a pair of retractor blades of a retractor toward a first vertebra and a second vertebra of a patient, fixing the retractor to the first vertebra with a first pin, moving the retractor blades away from each other, fixing the retractor to the second vertebra with a second pin, translating a distal portion of an interbody spacer insertion device toward the vertebrae along a longitudinal guide channel of the retractor blade, positioning an interbody spacer between the vertebrae of the patient, and disengaging the interbody spacer from the interbody spacer insertion device.

In aspects of the present disclosure, translating the interbody spacer insertion device may include translating an insertion guide along a fixed trajectory toward a disc space of the patient.

According to aspects of the present disclosure, the interbody spacer may be operably coupled to the interbody spacer insertion device.

In aspects of the present disclosure, operably coupling the interbody spacer may include moving a first arm of the interbody spacer insertion device from a first position to a second position away from a second arm of the interbody spacer, positioning the first arm about a plate, and moving the first arm back to the first position to engage the plate. The interbody spacer may be coupled to the plate. The plate may be coupled to the interbody spacer via a screw configured to rotatably engage a threaded aperture of the interbody spacer. The screw may be rotated in a first direction to release the screw from the interbody spacer. Force may be applied proximally to the interbody spacer insertion device to remove the interbody spacer insertion device from the patient.

According to aspects of the present disclosure, the first arm may be moved from the first position to the second position to move the first arm away from the second arm after removing the interbody spacer insertion device. The plate may be decoupled from the interbody spacer insertion device.

According to aspects of the present disclosure, a system for inserting an interbody spacer between vertebrae of a patient is disclosed. The system includes a retractor having a first retractor blade and a second retractor blade, the first and second retractor blades configured to move away from each other to retract tissue of a patient, a first pin configured to be fixed to a first vertebra of a patient, and an interbody spacer insertion device having a channel guide disposed thereon, the interbody spacer insertion device configured to slidably engage the first retractor blade during insertion of an interbody spacer. The first retractor blade may have a longitudinal guide channel configured to receive the channel guide of the interbody spacer insertion device therein. The first retractor blade may be a caudal retractor blade, a cephalad retractor blade or an auxiliary retractor blade oriented medially or laterally.

According to aspects, the interbody spacer insertion device is coupled to the longitudinal guide channel of the first retractor blade and translatable along a fixed trajectory toward the first and second vertebrae of the patient.

In aspects, the interbody spacer insertion device further includes a first arm and a second arm disposed along a distal portion of the interbody spacer insertion device, the first and second arms configured to move between a first configuration and a second configuration. In the first configuration, the first and second arms of the interbody spacer insertion device are approximated relative to one another, and in the second configuration, the first and second arms of the interbody spacer insertion device are expanded relative to one another. The interbody spacer insertion device may be configured to engage a plate coupled to the interbody spacer. The plate may be coupled to the interbody spacer via a screw configured to rotatably engage a threaded aperture of the interbody spacer.

According to aspects of the present disclosure, an expandable interbody spacer includes a first body portion and a second body portion rotatably coupled to the first body portion, such as via a rod, the first body portion having an engagement wall extending toward the second body portion. The expandable interbody spacer includes a pawl beam rotatably coupled to the second body portion via a pawl rod, and a plurality of teeth extending from the pawl beam. Transitioning the expandable interbody spacer from a closed configuration to an open configuration may cause the pawl beam to engage the plurality of teeth to prevent the expandable interbody spacer from transitioning to the closed configuration.

In aspects of the present disclosure, a method of placing an expandable interbody spacer includes advancing an expandable interbody spacer coupled to an interbody spacer insertion device toward vertebrae of a patient, the expandable interbody spacer maintained in a closed configuration by the expandable interbody spacer insertion device, positioning the expandable interbody spacer, in the closed configuration, between vertebrae of the patient, and releasing, with the interbody spacer insertion device, the expandable interbody spacer. Upon release, the expandable interbody spacer is configured to transition toward an open configuration to match a natural lordosis of the patient.

According to aspects, advancing includes advancing the interbody spacer insertion device along at least a portion of the longitudinal guide channel of a retractor blade. Advancing may include aligning a channel guide of the interbody spacer insertion device to the longitudinal guide channel of the retractor blade. The method may include moving or cutting the anterior longitudinal ligament ("ALL") of the patient after the expandable interbody spacer is positioned between and secured to the vertebrae, so that the expandable interbody spacer may be expanded or permitted to expand after the ALL is released prior to expanding the expandable interbody spacer.

In aspects of the present disclosure, a method of performing a surgical procedure is disclosed. The method may include advancing first and second of retractor blades of a retractor towards first and second vertebrae of a patient, fixing the first retractor blade to the first vertebra with a first pin, moving the first and second retractor blades away from each other, translating a distal portion of an interbody spacer insertion device towards the first and second vertebrae with a channel guide associated with the insertion device traversing along a longitudinal guide channel of one of the first or second retractor blades, positioning an interbody spacer associated with the insertion device between the first and second vertebrae of the patient, and disengaging the interbody spacer from the interbody spacer insertion device.

According to aspects, the second retractor blade may be fixed to the second vertebra with a second pin. The distal portion of the interbody spacer may include translating the insertion device with an interbody spacer/plate combination attached to the insertion device. The interbody spacer/plate combination may include an interbody spacer and a plate, the interbody spacer may have an attachment screw receiving hole, the plate may have an attachment bore for receiving an attachment screw inserted therethrough to secure the plate to the interbody spacer. Translating the distal portion of the interbody spacer insertion device may include translating the distal portion of the interbody spacer insertion device with the interbody spacer insertion device secured to the plate and the plate secured to an interbody spacer. The plate may define an axis passing through the attachment bore, the plate may have a pair of bone screw receiving holes with the center of each bone screw receiving hole offset from the axis. Each bone screw receiving hole may be offset from the axis on the same side of the axis. The center of each bone screw receiving hole may be offset from the axis by an angle of from about 5 degrees to about 30 degrees.

In aspects, the method may include inserting screws through the bone screw receiving holes to secure the interbody spacer to the first and second vertebrae. Disengaging the interbody spacer insertion device may include releasing the interbody spacer insertion device from the plate. The method may include removing the attachment screw from the plate and the interbody spacer. Translating the distal portion of the interbody spacer insertion device may include translating the distal portion of the interbody spacer insertion device with an expandable interbody spacer associated with the distal portion of the interbody spacer insertion device. Positioning the interbody spacer between the first and second vertebrae may include positioning the expandable interbody spacer between the first and second vertebrae in an unexpanded state.

According to aspects, screws may be inserted through bone screw receiving holes of the expandable interbody spacer to secure the expandable interbody spacer to the first and second vertebrae.

In aspects, the expandable interbody spacer may be released from the interbody spacer insertion device.

According to aspects, an anterior longitudinal ligament may be released after the expandable interbody spacer is secured to bone.

In aspects, the expandable interbody spacer may be expanded.

According to aspects, an auxiliary blade may be attached to the retractor.

In aspects, translating the distal portion of the interbody spacer insertion device includes engaging a channel guide associated with the distal portion of the interbody spacer insertion device with a longitudinal guide channel of the auxiliary blade and sliding the channel guide in the longitudinal guide channel.

According to an aspect of the present disclosure, a system for inserting an interbody spacer between vertebrae of a patient is disclosed. The system includes a retractor, a first pin, and an interbody spacer insertion device. The retractor has a first retractor blade and a second retractor blade, at least one of the first and second retractor blades has a longitudinal guide channel, the first and second retractor blades configured to move away from each other to retract tissue of a patient. The first pin is configured to be fixed to a first vertebra of a patient. The interbody spacer insertion device includes a channel guide disposed thereon, the channel guide configured to slidably engage the longitudinal guide channel during insertion of an interbody spacer, the interbody spacer insertion device configured to guide an interbody spacer releasably attached thereto into a space between the first and second vertebrae based upon the sliding engagement of the channel guide with the longitudinal guide channel.

In aspects, the interbody spacer insertion device is configured to releasably couple to a plate, the plate securable to the interbody spacer. The plate may have an attachment bore configured to receive an attachment screw to attach the plate to the interbody spacer. The plate may define an axis passing through the attachment bore, the plate may have a pair of bone screw receiving holes with the center of each bone screw receiving hole offset from the axis. The center of each bone screw receiving hole may be offset from the axis on the same side of the axis. The center of each bone screw receiving hole may be offset from the axis by an angle of from about 5 degrees to about 30 degrees.

According to aspects, the system may include an expandable interbody spacer releasably secured to a distal portion of the interbody spacer insertion device. The expandable interbody spacer may have an unexpanded state and an expanded state. The expandable interbody spacer may define a pivot axis and a pair of bone screw receiving holes, the pair of bone screw receiving holes being offset from a plane perpendicular to the pivot axis. The system may include an auxiliary blade securable to the retractor. The auxiliary blade may include a longitudinal guide channel, the channel guide being slidably engageable with the longitudinal guide channel of the auxiliary blade.

In an aspect of the present disclosure, an expandable interbody spacer is disclosed. The expandable interbody spacer includes a first body portion and a second body portion, a pawl beam, and a plurality of teeth extending from an engagement wall. The first body portion and the second body portion are pivotably coupled via a rod. Each of the first body portion and the second body portion defines a bone screw mount offset from a plane perpendicular to the pivot axis defined by the rod. Each bone screw mount includes a bone screw aperture. The pawl beam rotatably couples to the second body portion via a pawl rod. The plurality of teeth extending from the engagement wall is configured to engage the pawl beam. Transitioning the expandable interbody spacer from a closed configuration to an open configuration causes the pawl beam to engage the plurality of teeth to prevent the expandable interbody spacer from transitioning towards the closed configuration.

In aspects of the present disclosure, a combination of a plate and an interbody spacer includes an interbody spacer having an attachment screw receiving hole, and a plate. The plate defines an attachment bore for receiving an attachment screw inserted therethrough to secure the plate to the interbody spacer. The plate further defines an axis passing through the attachment bore and a pair of bone screw receiving holes with a center of each bone screw receiving hole offset from the axis.

According to aspects, the combination further includes a screw configured to extend through the attachment bore and engage the attachment screw receiving hole to secure the plate to the interbody spacer. The center of each bone screw receiving hole may be offset from the axis on the same side of the axis. The center of each bone screw receiving hole may be offset from the axis by an angle of from about 5 degrees to about 30 degrees.

BRIEF DESCRIPTION OF THE DRAWINGS

The accompanying drawings, which are incorporated in and constitute a part of the specification, illustrate embodiments of the disclosure and together with a general description of the disclosure given above, and the detailed description of the embodiment(s) given below, serve to explain the principles of the present disclosure.

FIG. 3A is a side view of a dissector for use with the retractor system of FIG. 1;

FIG. 3B is a cross-sectional view of the dissector of FIG. 3A;

FIG. 5E is a perspective view of the expandable interbody spacer of FIG. 5A in an open configuration;

FIG. 5F is an end view of the expandable interbody spacer of FIG. 5A in the open configuration;

FIG. 5G is a cross-sectional view of the expandable interbody spacer of FIG. 5A in the open configuration, taken along section line 5G-5G of FIG. 5E;

FIG. 8B is a perspective view of the expander of FIG. 8A engaging an expandable interbody spacer disposed between a first vertebra and a second vertebra;

FIG. 8C is a perspective view of the expandable interbody spacer disposed between the first and second vertebrae of FIG. 8B in a closed configuration;

FIG. 8D is a perspective view of the expandable interbody spacer disposed between the first and second vertebrae of FIG. 8B in an open configuration.

DETAILED DESCRIPTION

Figure 1:
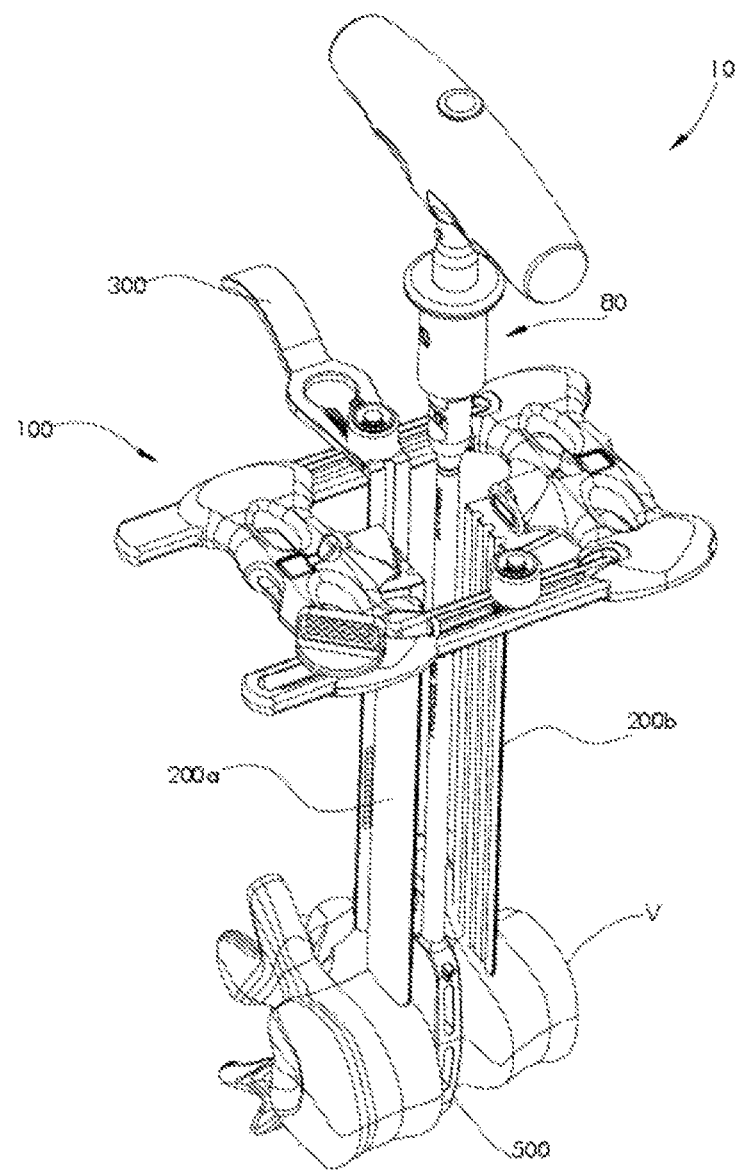
FIG. 1 is a perspective view of a retractor system provided in accordance with the present disclosure.

Embodiments of the presently described retractor systems and methods are described in detail with reference to the drawings, in which like or corresponding reference numerals designate identical or corresponding elements in each of the several views.

Reference will now be made to terms used throughout the present disclosure to describe the principles of the present disclosure. As used herein, the term "clinician" refers to a doctor, nurse, or other care providers and may include support personnel. As is traditional, the term "distal" refers to structure that is, in use, positioned farther from the clinician, whereas the term "proximal" refers to structure that is positioned closer to the clinician. Further, directional terms such as front, rear, upper, lower, top, bottom, distal, proximal, and the like are used to assist in understanding the description and are not intended to limit the present disclosure. The term "surgical field" refers to the space in which the surgical procedure is performed, and the term "surgical cavity" refers to a cavity at least partially surrounded by tissue.

Referring now to FIG. 1, a retractor system 10 is illustrated. The retractor system 10 includes a retractor 100, a first retractor blade 200a, a second retractor blade 200b, the first and second retractor blades 200a, 200b coupled to and extending distally from the retractor 100 forming an opening in tissue of a patient. The retractor 100 has an auxiliary blade 300 coupled thereon, the auxiliary blade 300 extending distally from the retractor 100. Retractor blades 200a, 200b may be oriented in a caudal-cephalad orientation with auxiliary blade positioned in a medial or lateral orientation. The retractor blades 200a, 200b have an interbody spacer insertion instrument 80 disposed between them with a spacer 500 coupled at a distal portion of the insertion instrument 80.

Figure 1A:
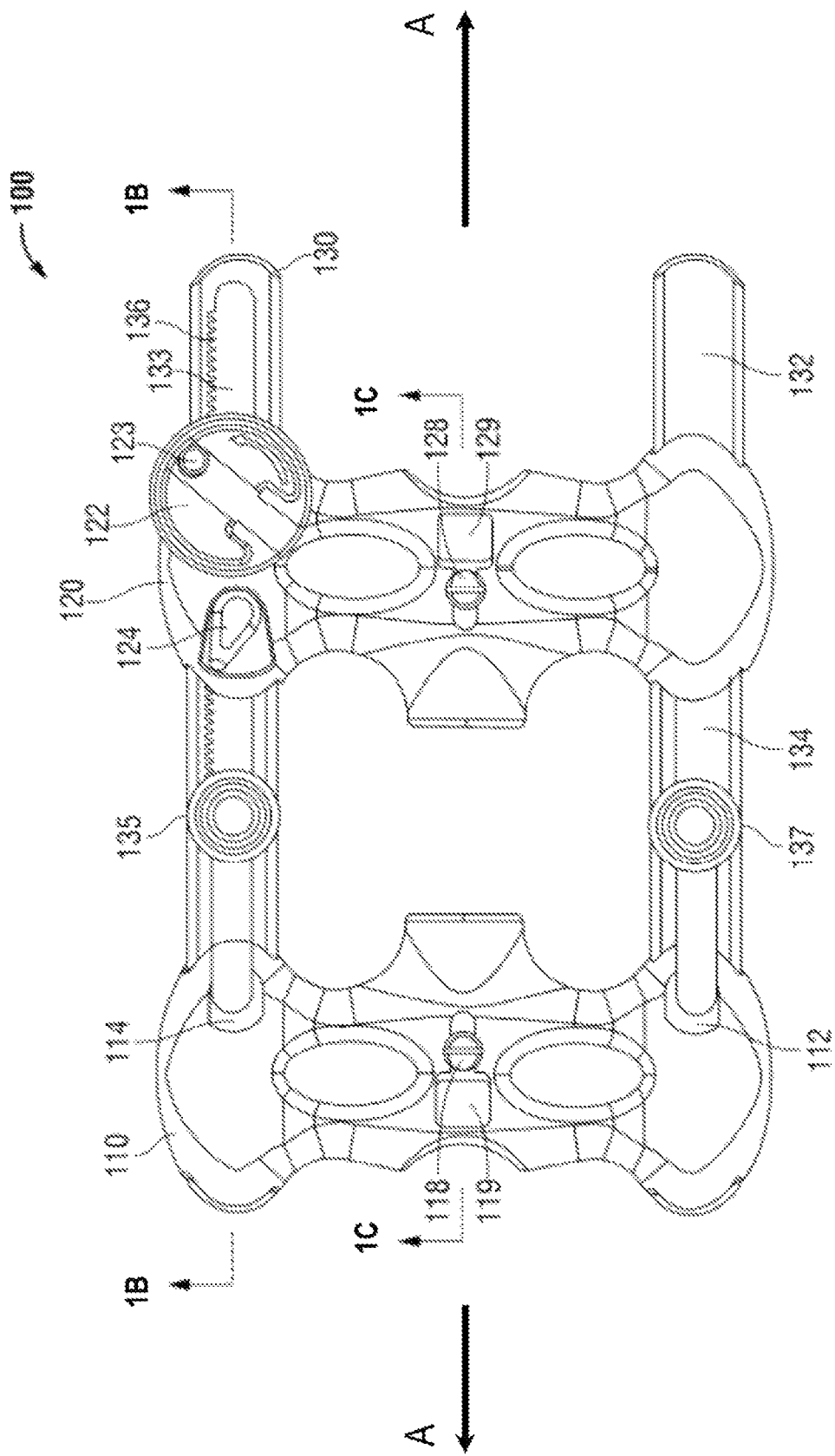
FIG. 1A is a top plan view of a retractor of the retractor system of FIG. 1.
Figure 1B:
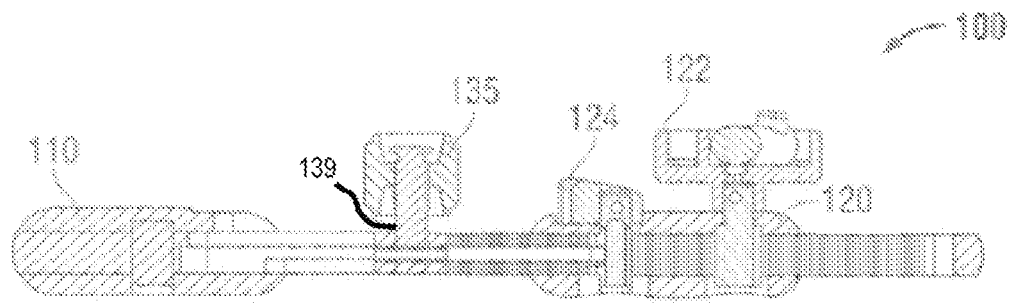
FIG. 1B is a side, cross-sectional view of the retractor of FIG. 1A taken along section line 1B-1B of FIG. 1A.
Figure 1C:
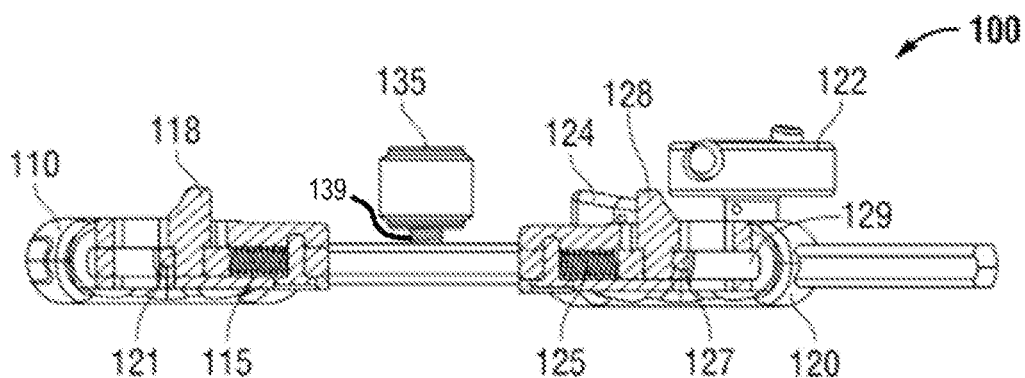
FIG. 1C is a side, cross-sectional view of the retractor system of FIG. 1A taken along section line 1C-1C in FIG. 1A.

Referring now to FIGS. 1A-1C, the retractor 100 is illustrated. The retractor 100 allows access to a target disc or target discs positioned between vertebrae "V" (FIG. 1), such as thoracic or lumbar vertebrae, and is referred to generally as retractor 100. The retractor 100 includes a first support 110 having arms 130, 132 extending from the first support 110. A second support 120 is configured to slidably receive and engage the arms 130, 132, enabling the second support 120 to operably couple to the first support 110 at a plurality of locations along the arms 130, 132. The first and second supports, 110, 120 are configured to receive and support retractor blades 200a, 200b (FIG. 2B) that, when assembled, extend distally from the respective supports 110, 120. In use, longitudinal movement of the second support 120 relative to the first support 110 along the arms 130, 132 allows longitudinal movement of the retractor blades 200a, 200b along an axis A-A. The retractor blades 200a, 200b are removably secured to the first and second supports 110, 120, though it is contemplated that, in embodiments, the retractor blades 200a, 200b may be permanently coupled to the first and second supports.

The arms 130, 132 of the retractor 100 define cavities 133, 134 that extend along an axis A-A at least partially along a length of the arms 130 132. The cavity 133 of the arm 130 includes teeth 136 that extend along an upper side of the arm 130, the teeth 136 are configured to operatively engage a translation knob 122 of the second support 120. In embodiments, it is contemplated that any portion of the surfaces defined by cavities 133, 134 may have teeth or other grooves disposed thereon that may be engaged by one or more translation knobs associated with each arm 130, 132, as desired. The translation knob 122 is configured to secure the second support 120 at a particular location on the arm 130 when the translation knob 122 is rotatably engaged. Additionally, the cavities 133, 134 are configured to accommodate locking wheels 135, 137 that are translatably disposed in respective cavities 133, 134. Each locking wheel 135, 137 is configured to secure an auxiliary blade 300 (FIG. 2C) at a position along the respective arm 130, 132.

With additional reference to FIG. 1, as noted above, the retractor blades 200a, 200b preferably are releasably attached to the first support 110 and the second support 120. An engaging arm 202 (FIGS. 2A, 2B) of each retractor blade 200a, 200b engages an underside of the first or second support 110, 120. The first and second supports 110, 120 define cavities 119, 129, that are configured to detachably secure the protruding portions 204 of the retractor blades 200a, 200b (FIGS. 2A, 2B) therein. Both the first and second supports 110, 120 include locking sliders 118, 128 that slidably engage the protruding portion 204 of the retractor blades 200a, 200b to releasably secure the protruding portions 204 of the retractor blades 200a, 200b within the cavities 119, 129. The locking sliders 118, 128 are operatively coupled to respective biasing members 115, 125 (FIG. 1C) such that the locking sliders 118, 128 are biased toward a locked state. Engaging portions 121, 127 (FIG. 1C) of the locking sliders 118, 128 engage grooves 206 (FIG. 2A, 2B) defined in protruding portions 204, thereby releasably securing the retractor blades 200a, 200b to the first support 110 and the second support 120. The first support 110 further defines a pair of recessed portions 112, 114 aligned with cavities 133, 134 and configured to accommodate respective locking wheels 135, 137 therein. The locking wheels 135, 137 allow approximation of the first and second supports 110, 120 to a closed cooperative position, with the locking wheels 135, 137 nested in the recessed portions 112, 114.

As noted above, the second support 120 includes a translation knob 122 that is rotatably mounted on, and configured to move, the second support 120 to a particular position along the arms 130, 132. A ratchet (not explicitly shown) engages the teeth 136 of the arm 130 as the first and second supports 110, 120 move away from one another. Similarly, when moving the second support 120 toward the first support 110, the translation knob 122 is rotated in the opposite direction when the ratchet is released. The second support 120 includes a ratchet assembly configured to allow uni-directional movement of the second support 120 and lock the second support in position along the arms 130, 132. The ratchet assembly includes a ratchet knob 124 configured to release and/or disengage the ratchet assembly with arm 130 to allow selective uni-directional movement of the second support 120.

Figure 2A:
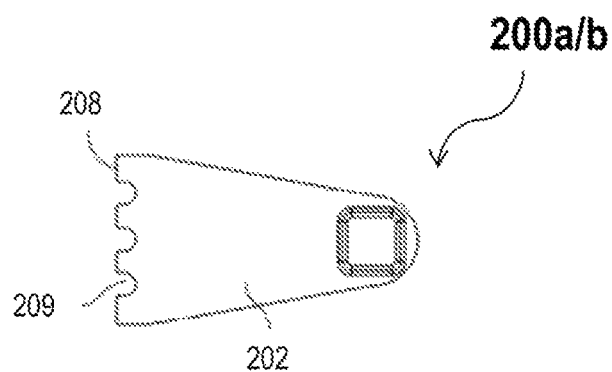
FIG. 2A is a top plan view of a retractor blade for use with the retractor of FIG. 1A.
Figure 2B:
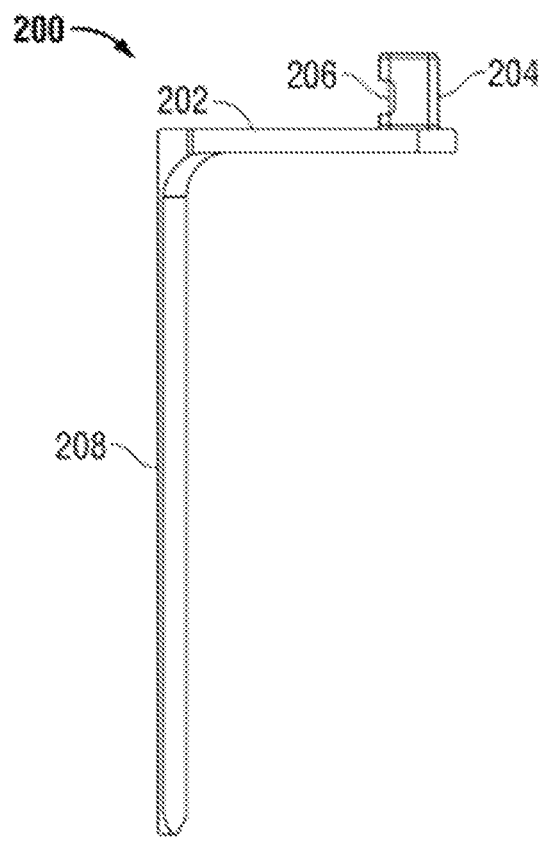
FIG. 2B is a side plan view of the retractor blade of FIG. 2A.

Referring now to FIGS. 2A and 2B, retractor blades 200a, 200b are configured to releasably couple to the first support 110 and the second support 120, respectively. Each retractor blade 200a, 200b has an engaging arm 202 and a blade portion 208 extending therefrom. The engaging arm 202 is configured to engage the underside of either the first or the second support 110, 120. The blade portion 208 is in substantially orthogonal relation to the engaging arm 202. By virtue of the relation of the blade portion 208 to the engaging arm 202, the blade portion 208 extends substantially orthogonally from the first or second support 110, 120 when assembled. It is contemplated that, in embodiments, the blade portion 208 may be coupled to the engaging arm 202 at varying angles such that the blade portion 208 may form a predetermined fixed angle with the engaging arm 202, and by extension, the first or second support 110, 120.

The engaging arm 202 includes a protruding portion 204 configured to extend through one of the cavities 119, 129 of the first or second support 110, 120, respectively. Specifically, each protruding portion 204 defines a groove 206 configured to securely engage the respective engaging portions 121, 127 (FIG. 1C) of the locking sliders 118, 128.

One or more longitudinal guide channels 209 extend substantially along the blade portion 208 distally from the engaging arm 202. The longitudinal guide channels 209 may extend along the entire length of the blade portion 208, though in embodiments the longitudinal guide channels 209 may extend distally a part of the way along the blade portion 208. In use, when the retractor blades 200a, 200b of the respective first and second supports 110, 120 are in close cooperative alignment, the opposing longitudinal guide channels 209 of the opposing blade portions 208 define one or more lumens configured to receive, for example, a guide wire, a guide pin, or other surgical implements therethrough (not shown). The longitudinal guide channels 209 may be rounded or may be shaped so as to form a semi-elliptical cross section to hold a pin in place therein (via e.g., a friction fit); the pin being removable when sufficient proximal force is applied. The distal portion of the blade portion 208 may form a concave profile adapted to engage and accommodate the contour of a vertebral body. In some embodiments, the concave recess defines a radius of curvature from about 0.1 inches to about 1.0 inches, and more preferably 0.6 inches. It is contemplated that, in embodiments, the clinician may select a retractor blade 200a or 200b having any particular radius of curvature as desired to accommodate varying vertebral bodies that are engaged by the retractor blade 200a or 200b.

Figure 2C:
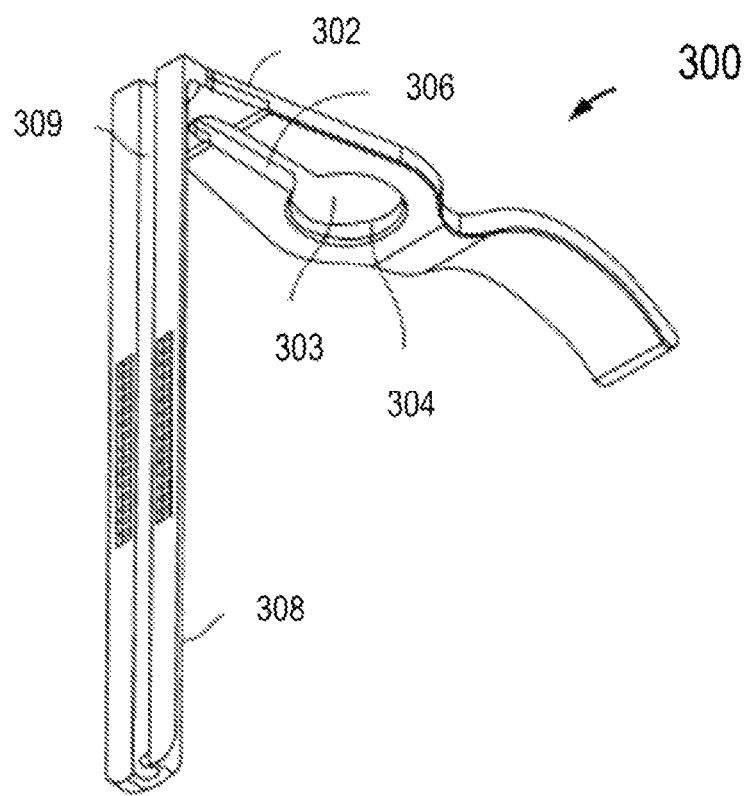
FIG. 2C is a perspective view of an auxiliary blade for use with the retractor of FIG. 1A.

Referring now to FIG. 2C, an auxiliary blade 300 is shown that is configured to couple to one of the arms 130, 132 of the retractor 100 in a medial or lateral position. The auxiliary blade 300 includes an engaging arm 302 defining an orifice 303 of varying dimensions and a blade portion 308 extending from the engaging arm 302. The orifice 303 of the engaging arm 302 is configured to be secured along the length of the arms 130, 132. More particularly, the orifice 303 defines an enlarged portion 304 and a narrowed portion 306 (e.g., a keyhole configuration). The enlarged portion 304 of the orifice 303 is configured to receive therethrough locking wheel 135, 137 of the first or second arm 130, 132, respectively, such that the engaging arm 302 of the auxiliary blade 300 may be positioned on one of the arms 130, 132 in a superimposed relation and secured by the respective locking wheel 135, 137. A neck portion 139 (FIG. 1B, 1C) of the locking wheel 135 is configured to be slidably received in the narrowed portion 306 of the auxiliary blade 300. A neck portion (not shown) of locking wheel 137 is similarly configured to be slidably received in the narrow portion 306 of the auxiliary blade 300. The blade portion 308 is substantially orthogonal with respect to the engaging arm 302, whereby when the auxiliary blade 300 is secured to one of the arms 130, 132, the blade portion 308 is substantially orthogonal to the respective arm 130, 132. Additionally, each blade portion 308 includes at least one longitudinal guide channel 309 extending substantially along the length of the blade portion 308, similar to the longitudinal guide channels 209 of the retractor blade 200. Likewise, similar to retractor blades 200a, 200b, the longitudinal guide channels 309 of the auxiliary blade 300 are configured to receive a guide wire, a guide pin, or other surgical implements therethrough.

Figure 6A:
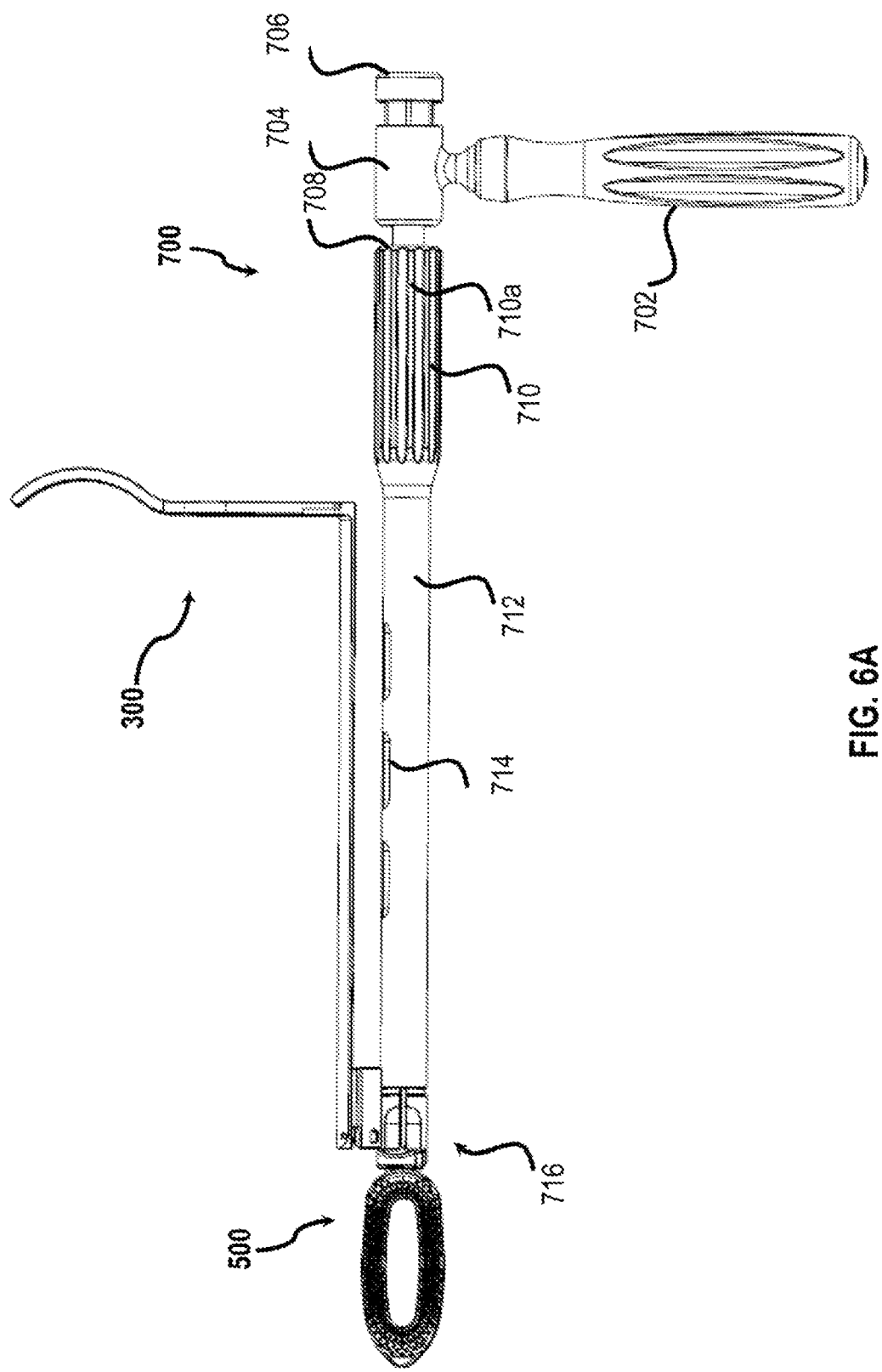
FIG. 6A is a side, plan view of an interbody spacer translation system for use with the retractor system of FIG. 1 or the retractor of FIG. 1A.
Figure 6B:
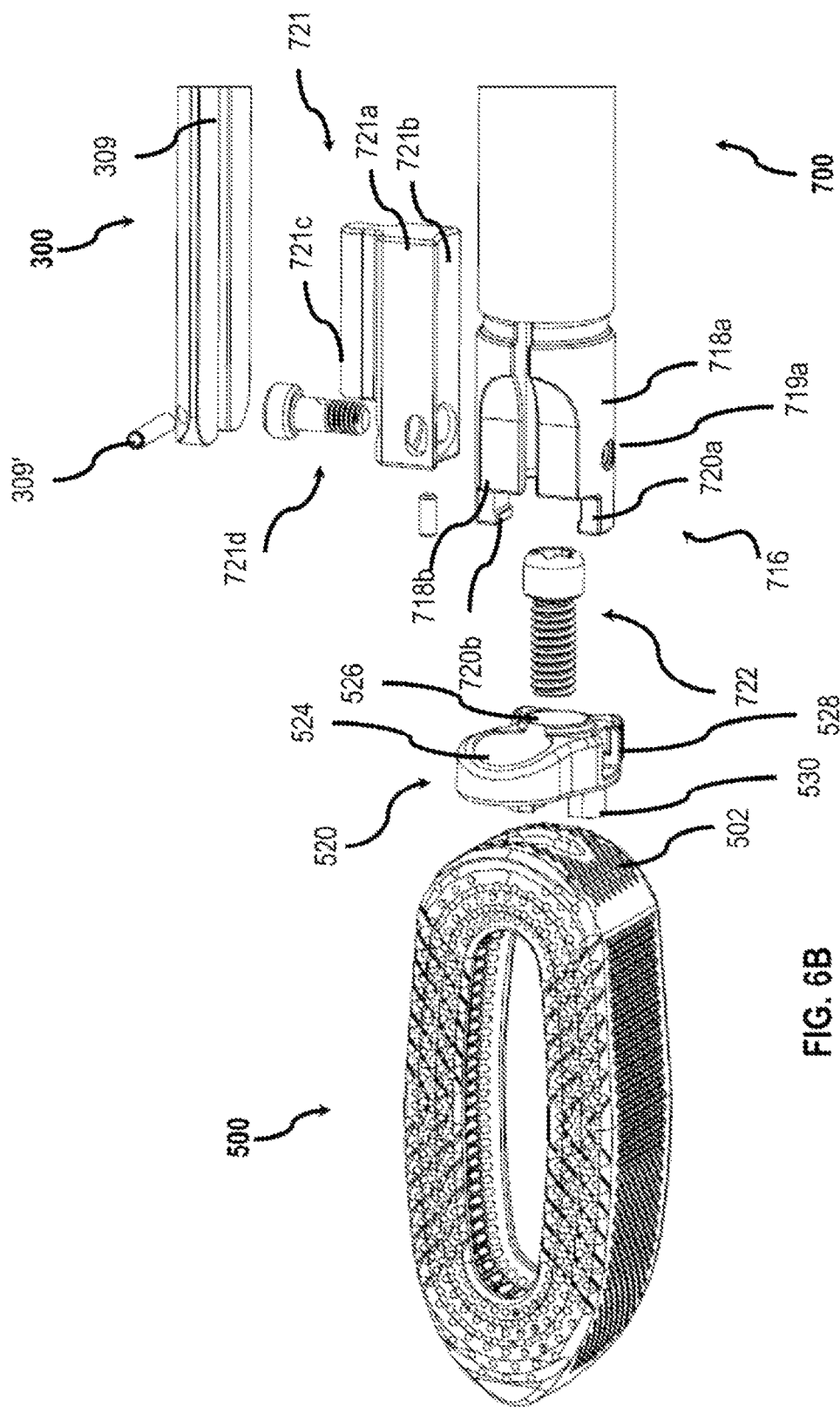
FIG. 6B is an exploded view of the distal portion of the interbody spacer translation system of FIG. 6A.

In embodiments, and with additional reference to FIG. 6B, the longitudinal guide channels 209, 309 of retractor blades 200a, 200b and/or auxiliary blade 300 are shaped to correspond to a shape of a channel guide 721c. The retractor blades 200a, 200b or auxiliary blade 300 may be configured to enable longitudinal translation of the insertion guides 721 through at least a portion of the longitudinal guide channel 209, 309 therealong. For example, the insertion guide 721, that is configured to couple to the insertion system 700, includes a channel guide 721c that further includes a neck portion and a rounded head portion. The neck portion and rounded head portion may be configured for slidable reception by the longitudinal guide channels 209, 309, each having a corresponding pattern formed along the surface of the longitudinal guide channels 209, 309. It will be understood that in such embodiments, the shape of the insertion guide 721 and corresponding longitudinal guide channels 209, 309 are keyed to control motion of the insertion system 700 and the implant associated with the insertion system so as to prevent unintended movement or "walking" of implants, plates, or combinations thereof during insertion between the vertebrae of patients. It will be further understood that the retractor blade 200 and/or the auxiliary blade 300 may be oriented in the cephalad direction (e.g., a cephalad blade), the caudal direction (e.g., a caudal blade), the posterior direction (e.g., a posterior blade) and the anterior direction (e.g., an anterior blade) to enable translation of insertion guides 721 along the respective portions of the patient as desired by the clinician, further allowing for increased flexibility. It is contemplated that the insertion guide 721 may be provided in a variety of sizes that allow the spacing between the auxiliary blade 300 (or blade 200) and the outer tubular member 712 of the insertion system 700 (FIG. 6A) to vary allowing increased flexibility in placement of the spacer 500 between adjacent vertebrae. Insertion guides 721 having a variety of sizes may be provided in a kit.

The auxiliary blade 300 may be adjustably secured to the arms 130, 132. Specifically, the neck portion 139 of the locking wheels 135, 137 may be slidably received through the narrowed portions 306 of the cavities 303 of corresponding auxiliary blades 300 to allow the clinician to position the auxiliary blades 300 in the transverse direction, as well as the longitudinal direction along the axis A-A along the arms 130, 132. Once positioned along one of the arms 130, 132 the clinician may rotate one of the locking wheels 135, 137 in a first direction to secure the auxiliary blade 300 to one of the arms 130, 132. To remove or reposition the auxiliary blade 300, the clinician may rotate one of the locking wheels 135, 137 in a second direction opposite the first direction, thereby partially or completely releasing the auxiliary blade 300 from one of the arms 130, 132.

Figure 2E:
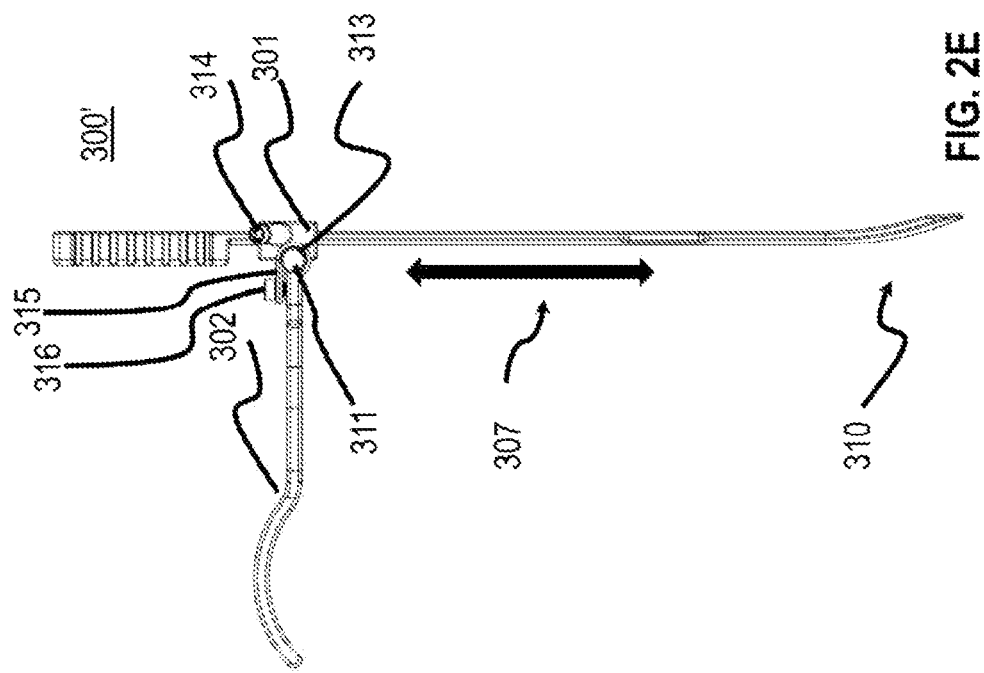
FIG. 2E is a side plan view of the auxiliary blade of FIG. 2D.
Figure 2D:
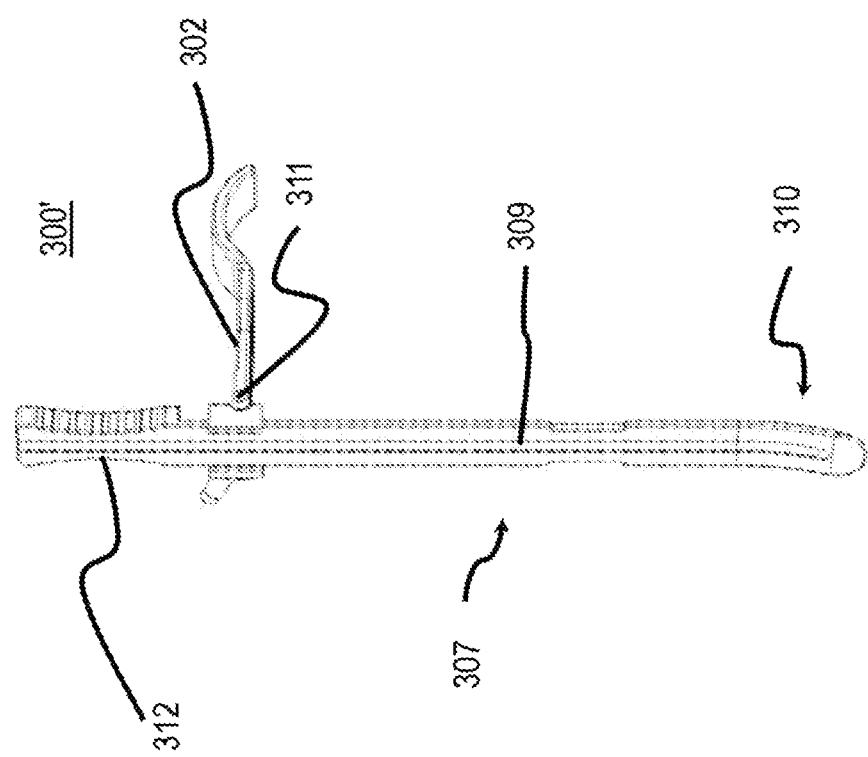
FIG. 2D is a perspective view of another embodiment of an auxiliary blade of the present disclosure.

Referring now to FIGS. 2D and 2E, an alternate embodiment of the auxiliary blade 300 of FIG. 2C is illustrated and referred to as curved blade 300'. The curved blade 300' is substantially similar to the auxiliary blade 300. The curved blade 300' includes a hand-grippable portion 312, a planar surface 307 extending distally from the hand-grippable portion 312, and an arcuate portion 310 extending distally from a distal portion of the planar surface 307. The planar surface 307 and the arcuate portion 310 are configured to slidably receive a shuttle 301. More particularly, the shuttle 301 includes a channel which receives the planar surface 307 and/or arcuate portion 310 therethrough. A shuttle pin 314 extends through the shuttle 301, and rotatably engages a bore (not explicitly shown) defining a threaded surface. Longitudinal guide channel 309 does not extend to the distal end of the auxiliary blade 300' as seen in FIG. 2D. This provides a limit stop such that an instrument traveling along the longitudinal guide channel 309 stops prior to reaching the distal end of the auxiliary blade 300'. In situations where a cutter (e.g., knife, scalpel, or other cutting instrument) is used to cut tissue (e.g., the ALL), the distal end of the longitudinal guide channel 309 limits how far the cutter travels along the auxiliary blade 300' into the working space such that the cutter is inhibited from cutting too far and risking damage to surrounding tissue and vasculature.

The planar surface 307 and the arcuate portion 310 have a longitudinal guide channel 309 extending along at least a portion of both the planar surface 307 and the arcuate portion 310. The arcuate portion 310 is defined in part by a predetermined radius of curvature. In use, when the curved blade 300' is introduced to a working channel of a patient to retract tissue, by virtue of the curvature of the arcuate portion 310 the tissue engaged by the arcuate portion 310 is retracted less than the tissue retracted by the planar surface 307. This may allow the clinician to retract the tissue located proximally farther than the tissue located distal to the clinician (when looking toward the vertebra of the patient), thereby reducing the chance for trauma to the distal tissue. The arcuate portion 310 of the curved blade 300' may also be shaped or toed inward such that, the arcuate portion 310 approximates the shape of the anterior portion of the vertebra when advanced toward the vertebra during surgical procedures. In embodiments, during surgical procedures, the distal portion of the curved blade 300' may be advanced such that the arcuate portion 310 extends along a side portion of the vertebra of the patient. The curved blade 300' further includes a cylindrical member 311 that rotatably couples the planar surface 307 to the engaging arm 302 within an engagement channel 313. The hand-grippable portion 312 of the curved blade 300' further includes a plurality of grooves or other ergonomic features disposed thereon to facilitate grip of the curved blade 300' by the clinician during surgical procedures.

To fix the shuttle 301 and the engaging arm 302 relative to the planar surface 307 or arcuate portion 310, the shuttle pin 314 is advanced inward until the shuttle pin 314 mechanically engages a side portion of either the planar surface 307 or arcuate portion 310. As such, the shuttle pin 314 enables selective positioning of the engaging arm 302 along the planar surface 307 or arcuate portion 310. When the shuttle pin 314 is retracted, it disengages from either the planar surface 307 or the arcuate portion 310, which allows the curved blade 300' to move up and down along the planar surface 307 and/or the arcuate portion 310 with respect to the engaging arm 302, thereby allowing the clinician to set the height at which the curved blade 300' is positioned with respect to the engaging arm 302. A toe screw 316 extends through an arm 315 extending from the shuttle 301. The toe screw 316 is configured to rotatably engage the engaging arm 302 to allow the engaging arm 302 to toe inwards or outwards relative to the planar surface 307. In embodiments, accessories may also be coupled to a shuttle (not shown) such as, without limitation, a light to the auxiliary blade 300 or curved blade 300'. In embodiments, the accessories may also be attached to the retractor blade 200.

Referring now to FIGS. 3A and 3B, a dissector 400 is illustrated for use with the retractor 100. While shown at a certain scale and as extending a predetermined marked distance, it will be understood that the dissector 400 may be formed to have a wider or narrower cross-section, and may be longer or shorter, depending on the particular needs of a clinician during a surgical procedure. The dissector 400 has a central passage 402 extending along the length of the dissector 400 with open proximal and distal portions. The central passage 402 is configured such that the dissector 400 may slidably receive a guide wire or guide pin therethrough (not shown). The guide wire or guide pin may guide the dissector 400 to the target disc of a patient during a surgical procedure. Additionally, the dissector 400 may have indicia marked (e.g., etched, printed or printed thereon) to indicate the depth of the body cavity or the distance between the epidermal tissue surface and the vertebral body. The clinician may use such indicia to select an appropriate retractor blade during the surgical procedure. In embodiments, the central passage 402 is defined by an electrically conductive tube with plastic over molded onto and surrounding the tube. A notch 404 is formed along the proximal portion of the dissector 400 in association with an electromyography system in a known manner. A clip from the electromyography system can be contacted with the conductive tube at the notch 404 with the signals transmitted along the tube inside the insulating plastic outer body, to the distal portion and/or distal tip of the conductive tube that contacts tissue.

Figure 4A:
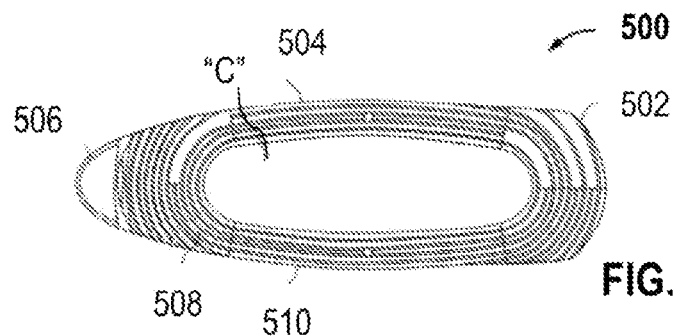
FIG. 4A is a top plan view of a spinal interbody spacer for use with the retractor system of FIG. 1.
Figure 4B:
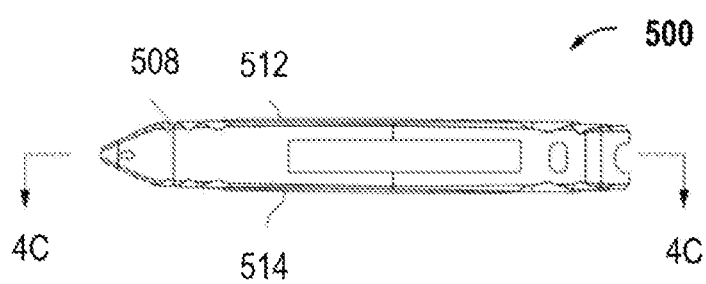
FIG. 4B is a side plan view of the spinal interbody spacer of FIG. 4A.
Figure 4C:
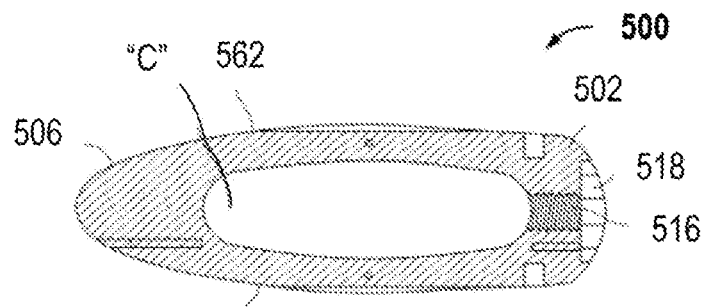
FIG. 4C is a cross-sectional view of the spinal interbody spacer of FIG. 4A taken along section line 4C-4C of FIG. 4B.

Referring now to FIGS. 4A-4C, a spinal interbody spacer or spacer 500 for placement between vertebrae is illustrated. The spacer 500 includes a pair of opposing side walls 510, 504, a blunt nose 506, and an arcuate proximal wall 502. The spacer 500 may be monolithically formed and may be made of any suitable biocompatible material such as, without limitation, polyetheretherketone ("PEEK"), polyphenylsulfonee (e.g., Radel®), polyetherimide (e.g., Ultem®), stainless steel, cobalt chrome, titanium, titanium alloys, and the like.

The spacer 500 defines a generally torpedo-shaped profile with an opening "C" extending therethrough to enable bone growth between adjacent vertebrae. Additionally, opening "C" is configured to accommodate additional bone graft material. The blunt nose 506 includes a substantially contoured, tapered surface to facilitate insertion thereof between the vertebral bodies. The spacer 500 includes a vertebral body engaging top and bottom surfaces 512, 514 having protrusions configured to facilitate gripping and securing of the spacer 500 with adjacent vertebrae. In particular, the protrusions include ring-patterned protrusions 508 concentrically arranged with respect to the opening "C". Additionally, the ring-patterned protrusions 508 of the opposing top and bottom surfaces 512, 514 may be configured to allow secure engagement with respect to each other when disposed in superposed relation. In embodiments discussed below, the interbody spacer may have opposing surfaces configured to expand upon mechanical engagement by an interbody spacer insertion system or insertion system 700 (FIGS. 6A, 6B) so as to enable the clinician to adjust the lordotic curvature of the patient once the interbody spacer is positioned between the vertebrae of the patient.

With continued reference to FIG. 4C, an arcuate proximal wall 502 includes a recess 518 defining a threaded aperture 516 for mating with an insertion system 700 (FIGS. 6A, 6B). The top and bottom surfaces 512, 514 of the spacer 500 are substantially parallel to one another. In embodiments, the top and bottom surfaces may be in angled relation. The spacer 500 may be tapered laterally and define a generally wedge shaped configuration. Specifically, one sidewall may have a height that is different from the height of the opposing sidewall defining the tapered or lordotic or hyperlordotic configuration. Alternatively, the opposing side walls may have the same height, and thus defining a parallel configuration.

For a detailed description of interbody spacers, including expandable interbody spacers, reference may be made to commonly owned U.S. Patent Application Publication No. 2017/0135824 entitled "Expandable Spinal Implant" and U.S. Pat. No. 9,468,535 entitled "Interbody Spacer" the contents of which are hereby incorporated by reference in their entirety.

Figure 4D:
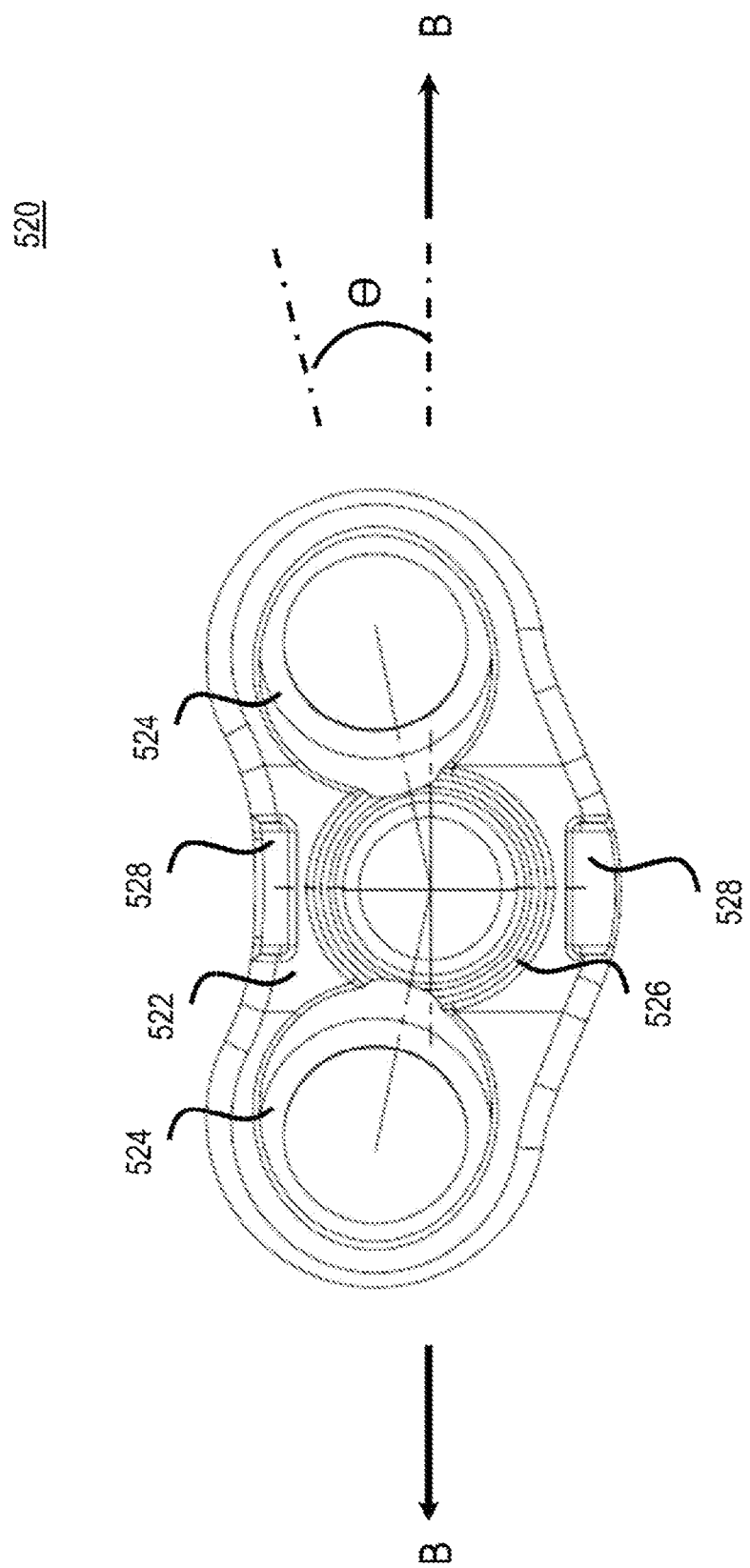
FIG. 4D is a top plan view of an interbody spacer attachment plate for use with the interbody spacer of FIG. 4A.

Referring now to FIG. 4D, an interbody spacer attachment plate or attachment plate 520 configured to couple to the spacer 500 (FIGS. 4A-4C) when fixing the spacer 500 to corresponding vertebrae is illustrated. The attachment plate 520 defines a pair of opposed surfaces 522 which extend along an axis B-B. A pair of screw bores 524 extends through the attachment plate 520 between openings in the opposed surfaces 522. The screw bores 524 are configured to receive bone screws (not shown) therein. The screw bores 524 are substantially circular. Each screw bore 524 has a center point and radius extending outward from the center point to an edge of the screw bore 524. An attachment bore 526 is interposed between the screw bores 524 and extends through the attachment plate 520. The attachment bore 526 has a center which is positioned along the B-B axis, and a radius extending from the center to a threaded surface configured to engage an attachment screw (not shown). In embodiments, the screw bores 524 and/or the attachment bore 526 may be tapered such that the radius of the bore decreases between pair of opposed surfaces 522 in a proximal to distal direction.

The respective centers of the screw bores 524 are offset relative to the center of the attachment bore 526 such that an angle θ is formed relative to the axis B-B. In particular, the screw bores 524 are offset in an anterior-posterior orientation such that the centers of the screw bores 524 define the angle θ with respect to the center of the attachment bore 526, which lies along the axis B-B. The angle θ may be anywhere from about 5 degrees to about 30 degrees, though in embodiments, it is contemplated that the angle may be any suitable angle between about 5 degrees and about 20 degrees. It will be appreciated that the angle θ need not be identical for each of the screw bores, and that one screw bore may be offset from axis B-B by a greater angle than the other screw bore. By virtue of the offset of the screw bores 524 relative to the attachment bore 526, the position of screw bores 524 is oriented in a direction so that anatomical structures (e.g., nerves, tissue and blood vessels) located on the side of the plate opposite to axis B-B from screw bores 524 are avoided, and the potential for damage to such structures as screws are inserted through the screw bores is minimized or reduced. In general, the screw bores are oriented in a posterior direction to avoid anteriorly oriented structures. Additionally, by virtue of the offset of the attachment bore 526 and pair of screw bores 524, the attachment plate 520 may be coupled to an implant (e.g., spacer 500 shown in FIGS. 4A-4C) while being positioned. Such positioning of the attachment plate 520 relative to the vertebrae of the patient provides the additional benefit of allowing the plate 520 to, when positioned in certain locations (e.g., along vertebrae associated with the lumbar part of the vertebral column) more closely approximate or match the curvature or lordosis of the associated vertebrae. For additional detail including an example of a suitable bone screw, reference may be made to commonly-owned U.S. Pat. No. 8,137,405, the contents of which are hereby incorporated by reference in their entirety.

Referring now to FIGS. 5A-5G, an expandable interbody spacer 600 is shown. The expandable interbody spacer 600 includes a first body portion 602 and a second body portion 604 configured to rotatably couple to the first body portion 602. The first and second body portions 602, 604 are rotatably coupled via a rod 606 so that the first body portion 602 and second body portion 604 pivot relative to one another about an axis B-B defined by the rod 606. The first body portion 602 and the second body portion 604 have a corresponding first bone screw mount 610 and a second bone screw mount 612 disposed at a proximal end of the first and second body portions 602, 604, respectively. In embodiments, the first and second bone screw mounts 610, 612 may be offset from a central portion of the expandable interbody spacer 600 when viewed from the proximal portion (e.g., the first and second bone screw mounts 610, 612 may be offset in the anterior or posterior directions) depending on the desired final position of the expandable interbody spacer 600. In embodiments where the first and second bone screw mounts 610, 612 are offset from the central portion of the expandable interbody spacer 600, such offset may be to increase the distance between the first and second bone screw mounts 610, 612 and tissue, nerves, or other anatomic features of the individual in the opposite direction. In particular, the first and second bone screw mounts 610, 612 may be disposed in a posterior direction as discussed in connection with the screw bores 524 of attachment plate 520 so that the screws are spaced from vessels and nerves disposed more anteriorly. A pawl beam 614 is rotatably coupled to the second body portion 604 and configured to engage an engagement wall 616 extending from the first body portion 602. For purposes of clarity, reference will be made to a left portion and a right portion of the expandable interbody spacer 600, and components associated therewith. The left portion is to be understood as referring to the portion of the expandable interbody spacer 600 configured to rotatably pivot during expansion of the expandable interbody spacer 600. The right portion of the expandable interbody spacer 600 is to be understood as referring to the portion of the expandable interbody spacer 600 configured to fix the orientation of the first body portion 602 relative to the second body portion 604 when the expandable interbody spacer 600 is expanded.

The first body portion 602 has an upper surface 620 having a plurality of protrusions 620a extending upward therefrom and a plurality of micro-apertures 620b. The protrusions 620a are configured to inhibit expulsion and/or movement of the expandable interbody spacer 600 by engaging an endplate of the vertebra adjacent the upper surface when the expandable interbody spacer 600 is positioned between adjacent vertebrae. The micro-apertures 620b extend from the upper surface 620 through the first body portion 602 downward to a lower surface (not explicitly shown) of the first body portion 602, and are configured to enable bone growth therethrough during spinal fusion of the vertebrae of the patient. The first body portion 602 further defines an opening 622 located centrally along the upper surface 620, the opening 622 extending downward from the upper surface 620 toward the second body portion 604. While the first body portion 602 and the opening 622 are shown forming a substantially elliptical shape, it will be understood that the aperture may take any variety of shapes (e.g., a circle, square, and the like). The opening 622 allows bone growth between adjacent vertebrae and also provides an area for packing the expandable interbody spacer 600 with bone growth material.

The first body portion 602 has the first bone screw mount 610 disposed along a proximal portion of the first body portion 602, the first bone screw mount 610 extending proximally and upward relative to the upper surface 620 of the first body portion 602. The first bone screw mount 610 defines an aperture 610a configured to receive a first bone screw washer 610b therein. The first bone screw washer 610b is made of a relative soft material (e.g., commercially pure titanium) configured to deform as a bone screw (not explicitly shown), formed of a harder material (e.g., titanium alloy Ti-6Al-4V), is inserted and engages the first bone screw washer 610b. The aperture 610a is angled so as to direct a screw inserted therethrough into the adjacent vertebral body.

Figure 5A:
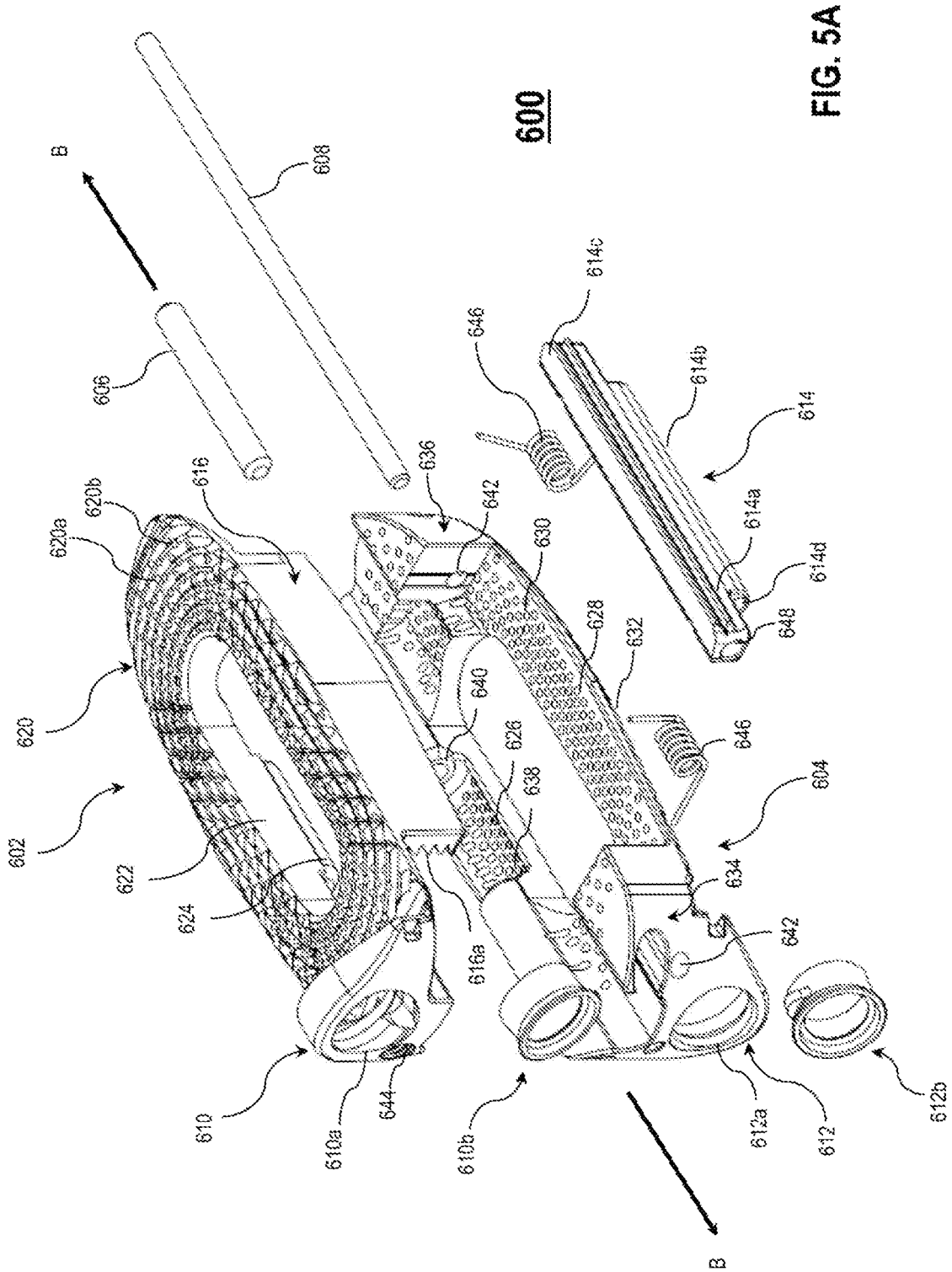
FIG. 5A is an exploded perspective view of an expandable interbody spacer according to embodiments of the present disclosure.

The first body portion 602 has a rotation cylinder 624 extending downward along a left portion of the first body portion 602. The rotation cylinder 624 is configured to receive the rod 606 therein to enable rotation about an axis B-B (FIG. 5A). More particularly, the rotation cylinder 624 is configured to mate with a curved indent 626 in the second body portion 604. The micro-apertures 620b which are aligned with the rotation cylinder 624 extend therethrough.

The first plate 602 has an engagement wall 616 extending downward from the right portion of the first body portion 602. The engagement wall 616 has teeth 616a extending distally from a proximal portion of the engagement wall 616. The teeth 616a further extend from the engagement wall 616 inward toward the aperture of the first and second body portions 602, 604. The teeth 616a of the engagement wall 616 are configured to engage teeth 614a of the pawl beam 614 to maintain the position of the first body portion 602 relative to the second body portion 604 when the expandable interbody spacer 600 is in an open configuration (FIG. 5G).

The second body portion 604 has an upper surface 628 including a plurality of micro-apertures 630 extending from the upper surface 620 of the second body portion 604 to a lower surface (not explicitly shown) of the second body portion 604. The second body portion 604 has a plurality of protrusions 632 extending downward from a lower surface (not explicitly shown) of the second body portion 604. Similar to the protrusions 620a of the first body portion 602, the protrusions 632 of the second body portion 604 are configured to inhibit expulsion and movement by the expandable interbody spacer 600 relative to the vertebrae of the patient by engaging an endplate of an adjacent vertebra.

Figure 5B:
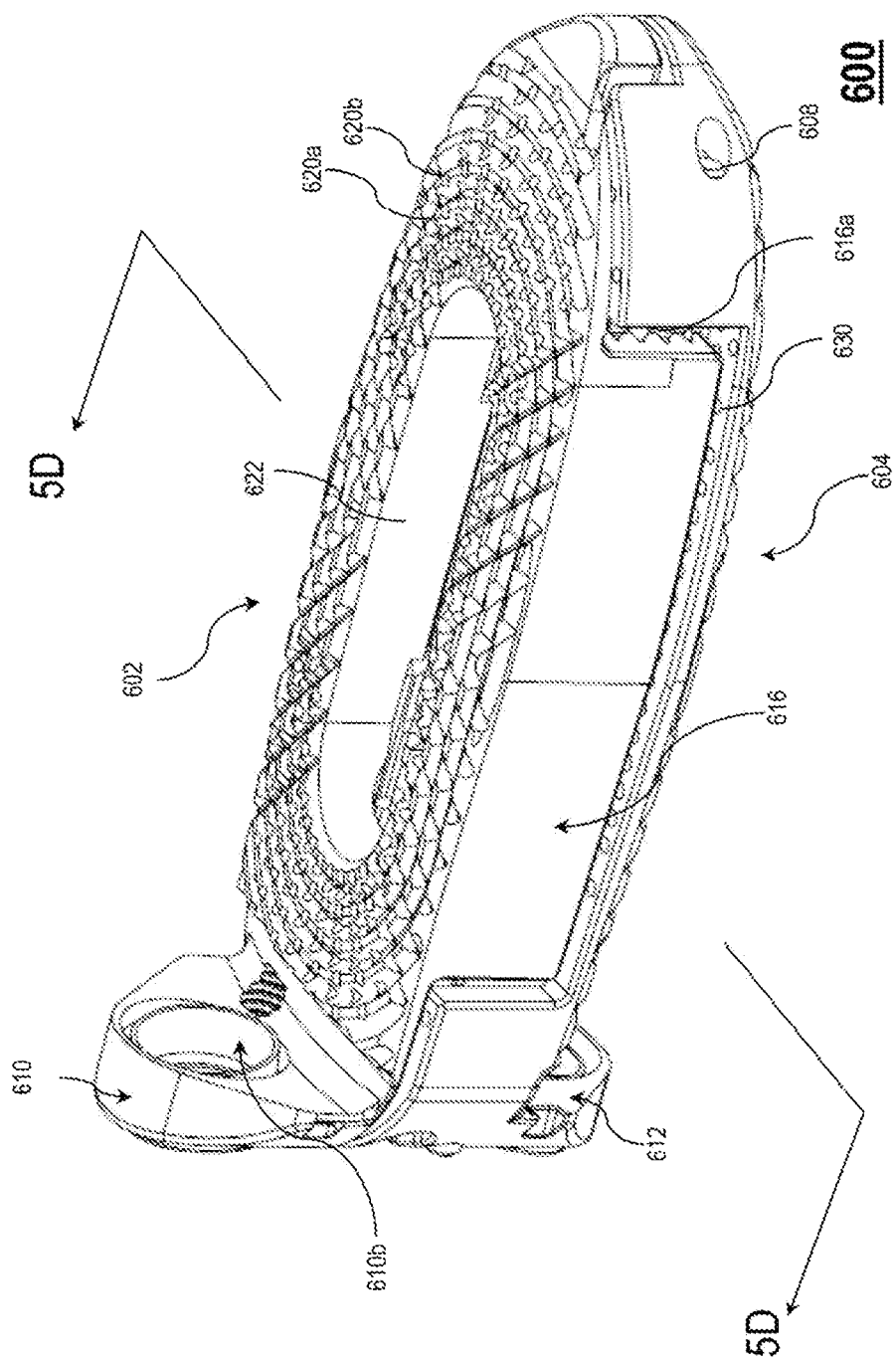
FIG. 5B is a perspective view of the expandable interbody spacer of FIG. 5A in a closed configuration.
Figure 5D:
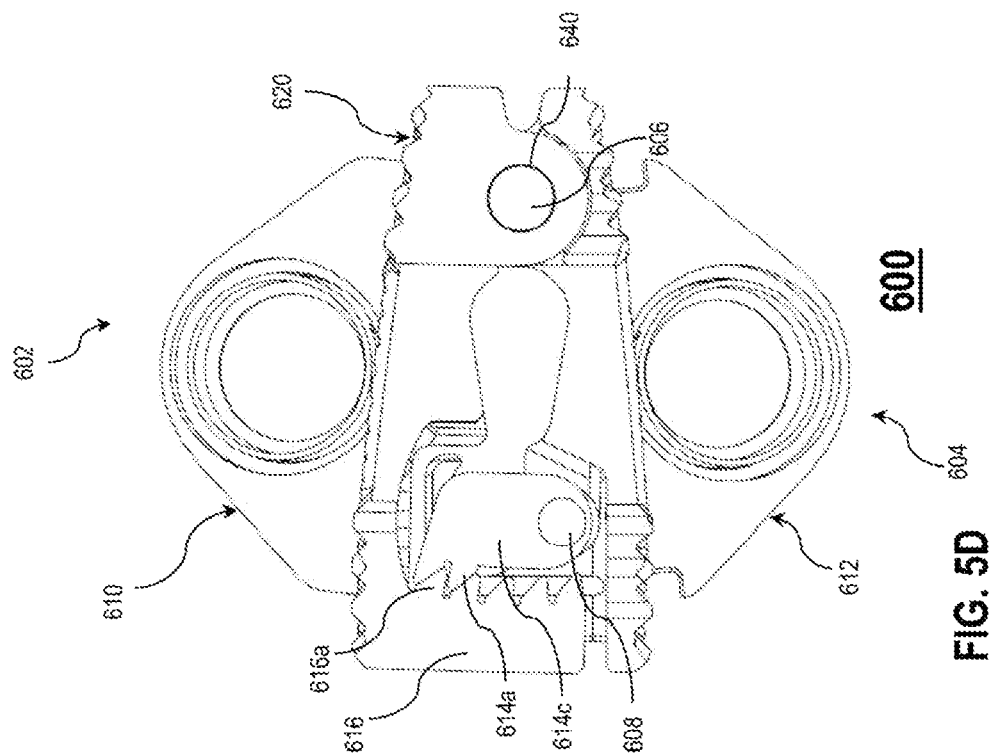
FIG. 5D is a cross-sectional view of the expandable interbody spacer of FIG. 5A in the closed configuration, taken along section line 5D-5D of FIG. 5B.
Figure 5C:
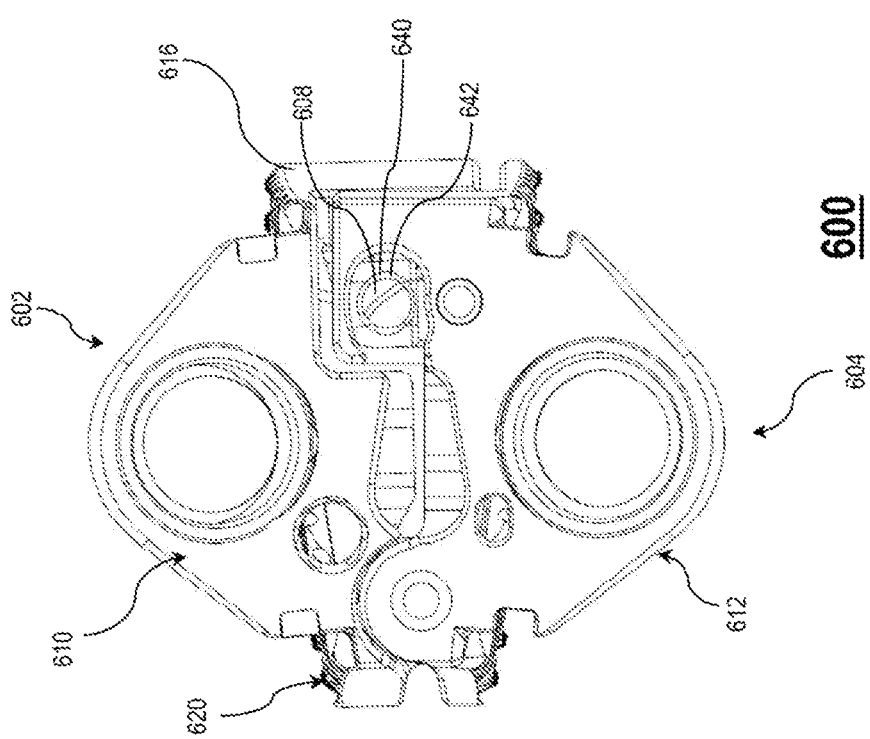
FIG. 5C is an end view of the expandable interbody spacer of FIG. 5A in the closed configuration.

In embodiments, the micro-apertures 620b of the first body portion 602 vertically align with the micro-apertures 630 of the second body portion 604 when in the closed configuration (FIG. 5B). The second body portion 604 has a proximal region 634 and a distal region 636 which extend from the upper surface 628 of the second body portion 604. The proximal and distal regions 634, 636 are configured to support the first body portion 602 when the expandable interbody spacer 600 is in the closed configuration (FIG. 5B), the first body portion 602 vertically offset from the second body portion 604.

The second body portion 604 has a curved indent or recess 638 which forms a surface disposed along the left portion of the second body portion 604 which, as noted above, is configured to mate with the rotation cylinder 624 of the first body portion 602. A pair of apertures 640 extends proximally and distally from the surface formed by the recess 638 to form corresponding bores through at least a portion of the proximal and distal regions 634, 636, respectively. The recess 638 is configured to rotatably receive the rotation cylinder 624 therein. The aperture 640 extending distal from the recess 638 extends to the distal portion of the second body portion 604, enabling insertion of the rotation cylinder 624 from the distal portion of the expandable interbody spacer 600. The apertures 640 are configured to receive the rod 606 for pivotally coupling the first body portion 602 and the second body portion 604.

Similarly, a pair of apertures 642 is disposed on opposing sides of a cavity formed by the proximal and distal regions 634, 636 along the right portion of the second body portion 604. The apertures 642 are in coaxial alignment and form corresponding bores which extend proximally and distally from the cavity through at least a portion of the proximal and distal regions 634, 636. The bore extending from the aperture of the distal region 636 extends to the distal portion of the distal region 636 and is configured to receive a pawl rod 608 therein.

The first body portion 602 has an aperture 644 disposed on the proximal portion of the first body portion. The aperture 644 defines a corresponding bore which extends distally through the first body portion 602. The bore has a threaded surface that is configured to receive a fixation screw (not shown) configured to couple the expandable interbody spacer 600 to an insertion tool (e.g., the insertion system 700 (FIG. 6A)).

The pawl rod 608 is configured to rotatably support the pawl beam 614 in the cavity formed between the proximal and distal regions 634, 636 of the second body portion 604. The pawl beam 614 includes a rotation beam 614b and an engagement beam 614c coupled to an upper surface of the rotation beam 614b. The rotation beam 614b has a pair of apertures 614d in coaxial alignment, the apertures 614d defining a bore extending through the rotation beam 614b. The bore extending through the rotation beam 614b is configured to receive the pawl rod 608 therein and enables rotatable engagement of the pawl beam 614 and the teeth 616a of the engagement wall 616. More particularly, the engagement beam 614c includes teeth 614a configured to engage the teeth 616a of the engagement wall 616 (FIGS. 5D and 5G) to maintain the orientation of the first body portion 602 relative to the second body portion 604 when in an expanded configuration (FIG. 5E). Coil springs 646 are configured to be positioned about proximal and distal portions of the pawl rod 608. The coil springs 646 are configured to apply rotational force to the engagement beam 614c to bias the pawl rod 608 outward toward the engagement wall 616 of the first body portion 602 to urge the teeth 614a into engagement with teeth 616a. The pawl rod 608 has a slot formed along the proximal end of the pawl rod 608 which is accessible through a bore defined by an aperture 648, the bore extending through the proximal region 634 of the second body portion 604.

Figure 9:
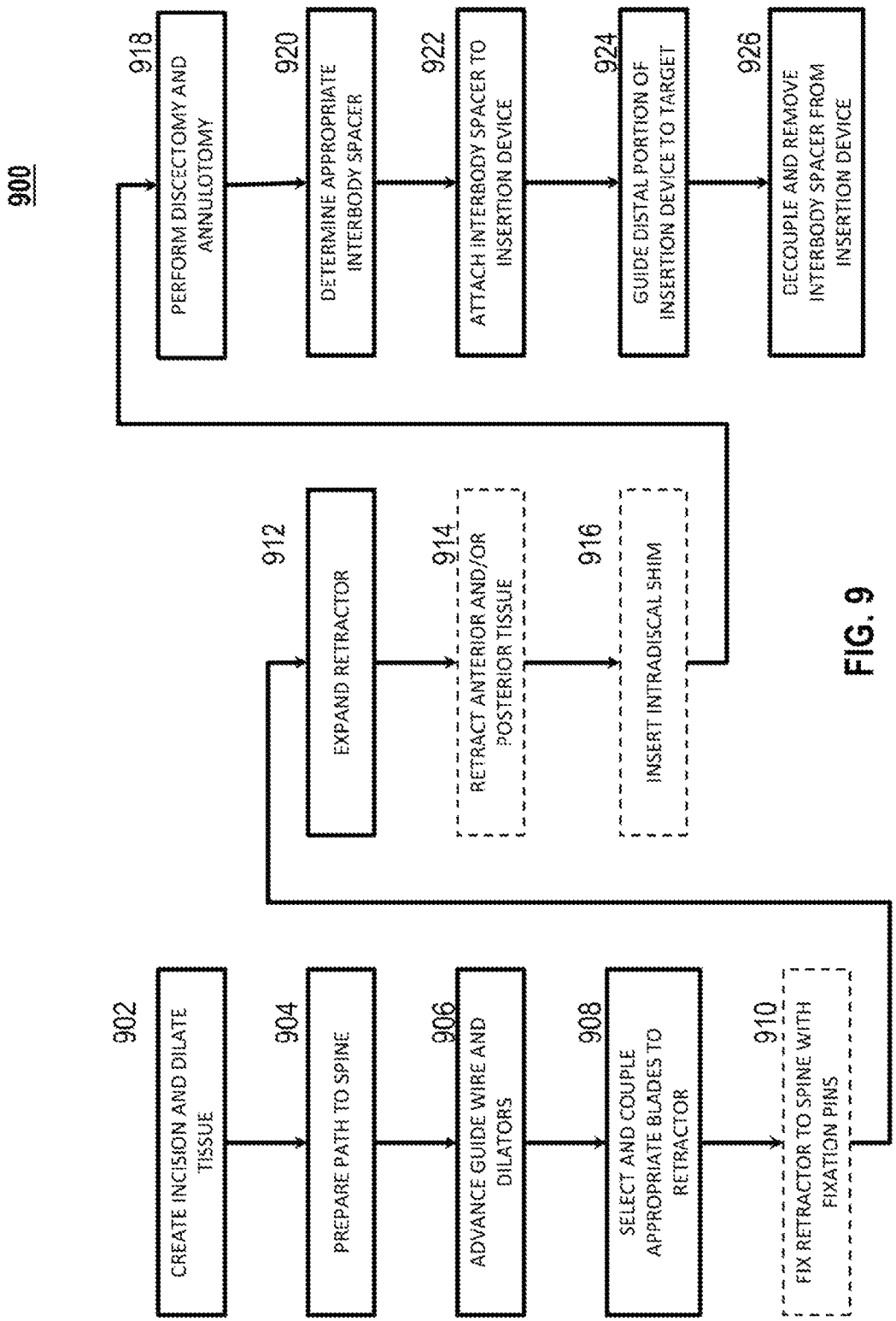
FIG. 9 is a flow diagram illustrating a method for retracting tissue and installing an interbody spacer between vertebrae of a patient.

The expandable interbody spacer 600 may be inserted between the vertebrae of a patient in conjunction with the retractor system 10 of FIG. 1 and/or in a manner similar to the method described with respect to FIG. 9. It is contemplated, however, that the expandable interbody spacer 600 may be inserted between the vertebrae by any other suitable method known in the art. In addition, the expandable interbody spacer 600 may be inserted without engaging the retractor 100 as discussed.

Once positioned between the first and second vertebrae, a first bone screw and a second bone screw, as are known in the art, are inserted through the first and second bone screw washers 610b, 612b that are positioned in the apertures 610a, 612a and into the adjacent vertebrae thereby rotatably coupling the expandable interbody spacer 600 to the first and second vertebrae of the patient. The first and second bone screws may be driven through pre-drilled holes established in the vertebrae of the patient. Alternatively, the first and second bone screws may be self-starting bone screws which do not require pre-drilling vertebrae before fixation thereto. As the first and second bone screws are inserted into the vertebrae, the first and second bone screws deform the corresponding bone screw washers 610*b*, 612*b*, fixing the first and second body portions 602, 604 to the respective vertebrae. Other structures known in the art, such as set screws, cover plates or washers, etc. are also contemplated for securing the screw to the implant.

With continued reference to FIGS. 5A-5G, and additional reference to FIGS. 8A-8D, engagement of the expandable interbody spacer 600 will be discussed in detail. Once inserted between the vertebrae of the patient and attached thereto, the first body portion 602 may be rotated relative to the second body portion 604 about the rod 606. To rotate the first body portion 602 relative to the second body portion 604, the blade 808 of the expander 800 (FIG. 8A) is inserted between the first and second body portions 602, 604. The expander 800 is rotatably engaged by a clinician to cause the edge 808*b* of the blade 808 to pivot about the rounded portion 808*a* in a first direction, causing the edge 808*b* to come into contact with the first body portion 602 of the expandable interbody spacer 600. As the expander 800 is rotated further, the first body portion 602 is rotated upward, causing the teeth 614*a* of the pawl beam 614 to ratchet and engage the teeth 616*a* of the engagement wall 616 of the first body portion 602. The ratcheting of the first body portion 602 relative to the second body portion 604 enables the clinician to transition the expandable interbody spacer 600 from a closed configuration (FIG. 5C) to an open configuration (FIG. 5E). Once in the open configuration, and more particularly when a desired amount of lordosis is established between first and second vertebrae of the patient, the expander 800 is rotated in a second direction different from the first direction, thereby causing the blade 808 of the expander 800 to disengage from the expandable interbody spacer 600. The teeth 616*a* of the engagement wall 616 rest on the teeth 614*a* of the pawl beam 614, thereby maintaining the position of the first body portion 602 relative to the second body portion 604 during spinal fusion of the vertebrae of the patient. This arrangement between the teeth 614*a* and the teeth 616*a* inhibits collapse of the expandable interbody spacer 600. Alternative modes of expanding the expandable interbody spacer also are contemplated. In the simplest aspect, the expandable interbody spacer may be permitted to passively expand as the patient is repositioned, with the expandable interbody spacer settling into a natural or desired position of lordosis based on patient positioning. In the alternative, the first and second body portions 602, 604 may be moved apart by expansion mechanisms such as a mechanical scissor jack, hydraulic expander or other known mechanisms.

It will be understood that, in embodiments, the coil springs 646 may be configured to apply an outward force such that when the expandable interbody spacer 600 is in a collapsed configuration, when released, the expandable interbody spacer 600 transitions to an open configuration (see FIG. 5E). More particularly, during a surgical procedure the expandable interbody spacer 600 may be locked or otherwise held in a closed configuration by the insertion system 700 prior to positioning between vertebrae of a patient. Once positioned as desired between vertebrae of a patient, the clinician positioning the expandable interbody spacer 600 may cause the insertion system 700 to release the expandable interbody spacer 600. Upon release, the first and second body portions 602, 604 may be urged to pivot about the rod 606 toward the open configuration, without being urged apart by the clinician. By allowing the expandable interbody spacer 600 to expand without the application of force by a clinician, an angle of lordosis maybe achieved without over or under expanding the expandable interbody spacer 600 by applying too much or too little rotational force.

Referring now to FIGS. 6A and 6B, illustrated is an interbody spacer translation system or insertion system 700 for positioning a spacer 500 between vertebrae of a patient during a surgical procedure. As will be described later in detail, the insertion system 700 is coupled to a spacer 500 and guided along one of the retractor blades 200, 300, 300'. While the insertion system 700 is shown slidably engaging the auxiliary blade 300, it will be apparent that the insertion system 700 may be positioned to engage and translate along the longitudinal guide channels 209 of the retractor blades 200*a*, 200*b*.

The insertion system 700 includes a housing 704 defining a bore that is configured to slidably receive an inner tubular member 708 therethrough. When assembled, a handle 702 of the housing 704 is in orthogonal relation with the inner tubular member 708 extending distally therefrom. The housing 704 includes a proximal portion configured to receive a release assembly 706 that releasably couples to the inner tubular member 708.

The inner tubular member 708 extends distally from the housing 704 through a bore defined by an outer tubular member 712. The outer tubular member 712 has a hand-grippable portion 710 with a bore extending therethrough coupled proximally to the outer tubular member 712. In embodiments, the hand-grippable portion 710 includes a plurality of ribs 710*a*, or other ergonomic features that enhance gripping the hand-grippable portion 710, extending outward about the hand-grippable portion 710 to allow the clinician to grip and rotate the hand-grippable portion 710. The outer tubular member 712 may have one or more windows 714 disposed along the outer tubular member 712 and extending therethrough to allow visual inspection of the inner tubular member 708 when inserted through the outer tubular member 712. More particularly, the windows 714 may allow visual inspection of indicia or instrument features of instruments disposed within the bore of the outer tubular member 712 such as, for example, the inner tubular member 708. The windows 714 also may facilitate cleaning and sterilization of the instrument between uses.

The distal portion of the inner tubular member 708 has a coupling 716 disposed at the end thereof. The coupling 716 is configured to be rotatably engaged by either the hand-grippable portion 710 or the release assembly 706. More particularly, counter-clockwise rotation of the hand-grippable portion 710 causes the outer tubular member 712 to rotatably engage the coupling 716, causing arms 718*a*, 718*b* to move away from one another. Conversely, clockwise rotation of the hand-grippable portion 710 when the arms 718*a*, 718*b* are in an expanded configuration causes the arms 718*a*, 718*b* to move toward one another. Such movement of the arms 718*a*, 718*b* towards and away and from one another allows the arms 718*a*, 718*b* to engage the attachment plate 520 (FIG. 4D) or the expandable interbody spacer 600 (FIG. 5A).

With particular reference to FIG. 6B, the distal portion of the insertion system 700 is shown, with parts separated. The coupling 716 has two arms 718*a*, 718*b* in opposed relation. The arms 718*a*, 718*b* are biased inwards relative to the inner tubular member 708 and couple to an internal actuation assembly (not shown) that by default maintains the arms 718a, 718b in a close cooperative position relative to one another. When the release assembly 706 is engaged, the arms 718a, 718b are moved away from each other. This outward motion expands the distance between a first hook 720a and a second hook 720b. A screw engagement mechanism (not shown) has an engagement portion that is configured to be received in an opening of a screw 722. The screw engagement mechanism may be a tubular member that extends through a bore defined by the inner tubular member 708 and may rotate either independent of the inner tubular member 708 or in concert with the inner tubular member 708. In embodiments, the screw engagement mechanism may advance proximally or distally to advance the screw 722 toward or away from the spacer 500.

The screw 722 includes a head with a recess configured to receive the screw engagement mechanism therein, and a threaded portion extending distally from the head. The threaded portion is configured to extend through the attachment plate 520 (FIG. 4D). As discussed hereinabove, the plate 520 has a top surface defining the attachment bore 526 extending through the attachment plate 520 distally toward the bottom surface, an offset pair of screw bores 524 configured to receive bone screws (not shown) therein, and a periphery extending distally from the top surface to a bottom surface. The periphery has a pair of indents 528 extending inward along the periphery of the attachment plate 520. The indents 528 form an L shape indent configured to slidably receive the arms 718a, 718b when the arms are in an approximated configuration. The bottom surface has a pair of flanges 530 (FIG. 6B) extending distally from the attachment plate 520, the flanges 530 are configured to slidably engage the recess 518 of the spacer 500. In embodiments, the flanges 530 may be configured to approximate the shape of the recess 518 of the spacer 500.

Prior to insertion of the spacer 500 between vertebrae of a patient, the screw 722 may be inserted and advanced distally through the attachment plate 520. Once advanced through the attachment plate 520, the threaded portion of the screw 722 may rotatably engage the threaded aperture 516 of the spacer 500 to secure the attachment plate 520 to the spacer 500.

To couple the coupling 716 to the attachment plate 520, thereby operably coupling the insertion system 700 to the spacer 500, the actuation assembly (not shown) may be actuated by a clinician, thereby causing the arms 718a, 718b to expand outward. The arms 718a, 718b may be advanced such that the first and second hooks 720a, 720b are aligned with the opposing indents 528 of the attachment plate 520. Upon release of the actuation assembly, the arms 718a, 718b, and, by extension, the corresponding first and second hooks 720a, 720b, advance inwards into the indents 528, thereby securing the attachment plate 520 to the insertion system 700. In the alternative, arms 718a, 718b may be biased apart, with the actuation mechanism compressing the arms together, such as with a compression tube, to grasp and hold the implant. As will be appreciated, the inserter may be configured in the alternative to engage the expandable interbody spacer 600, as discussed herein.

With continued reference to FIG. 6B, an insertion guide 721 may be coupled to the insertion system 700 to guide the insertion system 700 along the longitudinal guide channel 209 defined by the retractor blade 200a, 200b or the longitudinal guide channel 309 defined by the auxiliary blade 300. The insertion guide 721 has a chassis 721a having an arcuate surface 721b and a channel guide 721c. The arcuate surface 721b is configured to approximate an outer surface of either arm 718a, 718b and/or the outer surface of the outer tubular member 712. The channel guide 721c extends outward from the chassis 721a and forms a pair of concave surfaces that invert and form a convex head. The convex head of the channel guide 721c is configured to slidably engage the longitudinal guide channel 309 defined by the auxiliary blade 300. The insertion guide 721 is coupled to the first or second arm 718a, 718b via a screw 721d. More particularly, the screw is configured to extend through a bore defined by the chassis 721a of the insertion guide 721 and a threaded aperture 719a, 719b of the corresponding arm 718a, 718b. Alternatively, the insertion guide 721 may be integrally formed with a portion of the insertion device 700, or may be welded or otherwise attached thereto by suitable means. In addition, other keyed shapes of engagement between the insertion guide 721 and the retractor blades 200a, 200b is contemplated, such as a dovetail joint.

The distal portion of the auxiliary blade 300 has a transverse bore extending at least partially therethrough, the transverse bore configured to receive a pin 309' therein. The pin 309' may be made of tantalum or any other substance known in the art that provides a clear indication of the position of the pin 309', and by extension the position of the auxiliary blade 300, in a fluoroscopic image captured during fluoroscopic imaging of the auxiliary blade 300.

Figure 7:
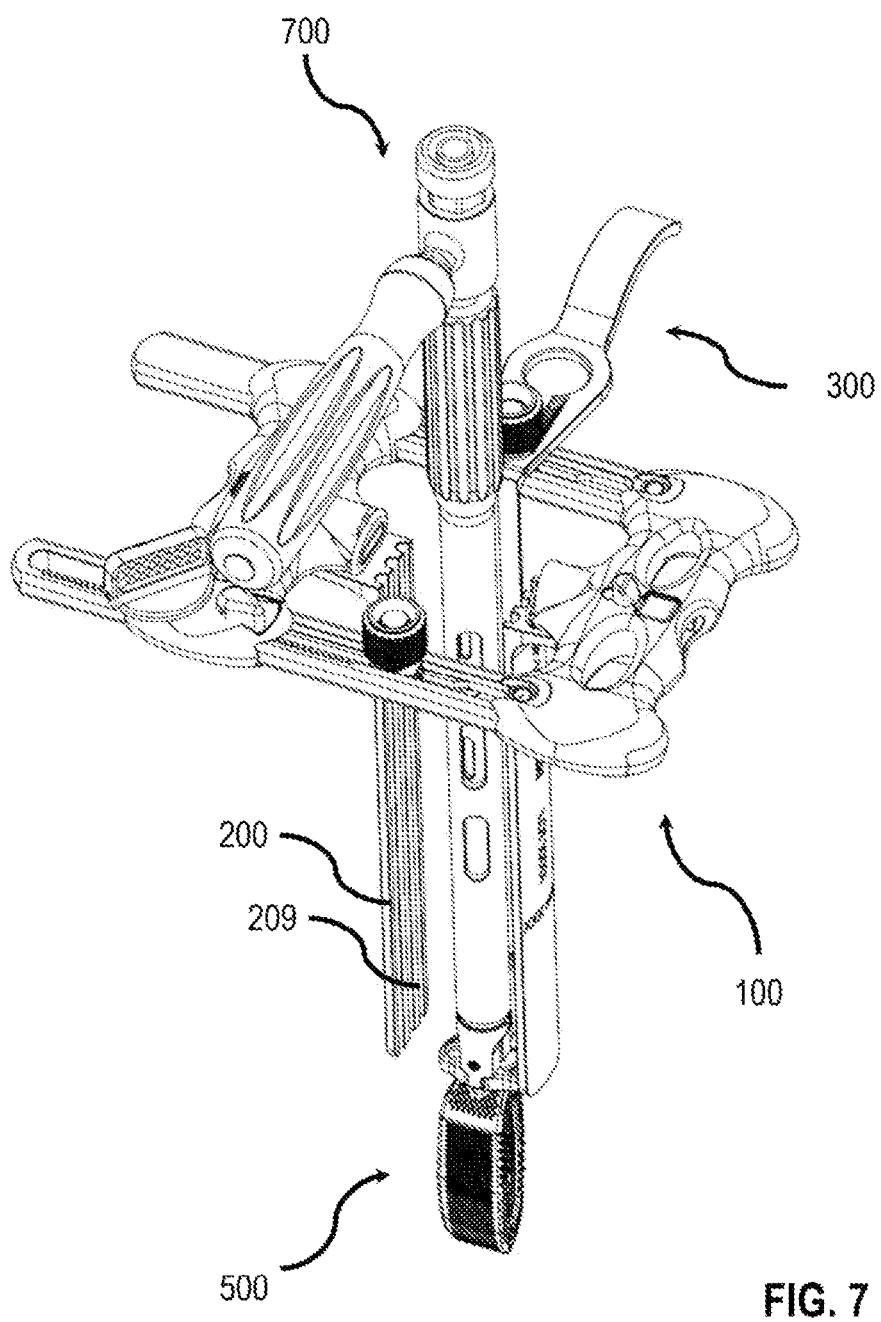
FIG. 7 is a perspective view of interbody spacer translation system of FIG. 6A engaging the retractor of FIG. 1A.

Referring now to FIG. 7, illustrating the insertion system 700 engaging the retractor system 10 of FIG. 1, discussed is a method described with reference to FIG. 9 that details an illustrative example of a method for replacing a damaged intervertebral disc by the retractor system 10. While reference will be made to the insertion of the spacer 500 in connection with the retractor 100, it will be understood that the expandable interbody spacer 600 may be inserted in a similar manner. It will also be understood by one skilled in the art that the expandable interbody spacer 600 may be inserted with an insertion system (e.g., insertion system 700), without slidably engaging the longitudinal guide channels 209 of the retractor blades 200a, 200b or the longitudinal guide channel 309 of the auxiliary blade 300 when guiding the expandable interbody spacer 600 toward the vertebrae of a patient. In this regard, it will be understood that the insertion system 700 may be used during surgical procedures with retractors known in the art, or during procedures without the use of a retractor.

In use, a clinician positions a patient in a lateral decubitus position with the iliac crest of the patient located directly over a table break. The patient is then secured typically via straps or other known tensioning devices, just below the iliac crest and over the thoracic region of the patient. The legs are likewise secured to the table, so as to prevent movement of the patient during the surgical procedure. Once secured, fluoroscopic images of the patient are captured to obtain images of the targeted disc or discs for replacement.

Referring now to FIG. 9, once the clinician is satisfied with the placement of the patient and the obtained fluoroscopic images, an incision is made (block 902). In embodiments, when replacing one disc, a transverse incision is made, and when replacing multiple discs, a vertical incision is made relative to the patient, to provide subcutaneous access to the iliac portion of the patient. Once the desired incision is created, the exposed muscle fibers are separated by the clinician as the clinician advances a finger into the retroperitoneal space of the patient. The peritoneum is released anteriorly as the retroperitoneal space is developed, allowing the clinician to gain access to the psoas muscle and/or the anterior tip of the transverse process. Once the clinician verifies development of the retroperitoneal space, a dissector is inserted, advanced through the psoas muscle, and fixed directly to the middle of an intervertebral disc or target disc. The clinician may move the dissector as desired to free soft tissue surrounding the target disc, completing preparation of the path to the spine of the patient (block 904).

Once the path is established at block 904, an intradiscal guidewire is placed through the dissector and advanced into the disc of the patient. If additional dilation is desired by the clinician, the first dilator may be removed, and a second dilator may be introduced in the place of the first dilator. The second dilator, larger than the first, is guided to the target disc by following the path along the guidewire, keeping the second dilator in line with the muscle fibers of the psoas and safely anterior to the lumbar plexus. The clinician may move the proximal portion of the first and/or second dilator back and forth to further develop the surgical site (block 906). Once the dilator is seated in place as desired by the clinician, a measurement may be taken of the exterior tissue or skin of the patient relative to the first or second dilator so as to allow the clinician to select an appropriate pair of retractor blades (e.g., retractor blades that are at the appropriate length) (block 908). Once selected, the corresponding retractor blades are attached to the retractor 100. The retractor 100 may be closed such that the retractor blades 200*a*, 200*b* are in close cooperative alignment. After removing the first or second dilator, the retractor 100 is inserted into the tissue and advanced toward the target disc and associated vertebrae. When the retractor is in position, the retractor 100 is rotated 90 degrees prior to expansion. Optionally, one or more pins may be inserted through the longitudinal guide channels 209 of the retractor blades 200*a*, 200*b* once rotated and fixed to the vertebrae of the patient (block 910). In an embodiment, a pin is inserted into the channel of one retractor and anchored in the bone of one vertebra.

Once in place, and optionally secured, the retractor 100 is expanded (block 912). In the case where one pin is inserted into the groove of one blade (e.g., the first retractor blade 200*a*), expanding the retractor 100 causes the other blade (e.g., the second retractor blade 200*b*) to move away from the first retractor blade (200*a*) which is fixed by the pin. Once the retractor 100 has been expanded, the guidewire may be removed, and the retractor 100 expanded further, as desired by the clinician. As desired, where one or no pin has been used, additional fixation pins may be secured to the vertebrae as desired by the clinician. If additional, transverse, retraction is desired, the auxiliary blades 300 may be inserted and coupled to the retractor 100. Once inserted, the auxiliary blades 300 may be expanded outward, retracting the corresponding tissue (block 914). An intradiscal shim (not shown) may be inserted as desired to prevent or reduce the chance of soft tissue creep into a working channel of the surgical site during the surgical procedure (block 916). For additional support, a table-mounted surgical arm (not shown) may be attached to the retractor 100 to maintain the position of the retractor assembly relative to the surgical table, and by extension, the patient.

Once the working channel is established, a traditional annulotomy and discectomy are performed (block 918). The annulotomy and discectomy are performed by first determining an appropriate interbody spacer, or sequence of spacers, to distract the space occupied by the target disc (block 920.) In embodiments, trial interbody spacers may be inserted and placed in between the vertebrae (e.g., by advancing the trial interbody spacer with a slap-hammer) to facilitate selection of a spacer 500 that is appropriate.

When placing the spacer 500 selected by the clinician, the spacer 500 is threadably coupled to the insertion system 700 via the attachment plate 520 (block 922). This allows the clinician to insert the spacer 500 and attachment plate 520 into the intervertebral space as a single unit. Alternatively, the spacer 500 may be inserted into the intervertebral space first and the attachment plate 520 is coupled to the spacer 500 subsequent to placement in the intervertebral space. During placement, a handle 702 may be used (or, where necessary, a slap-hammer (not shown) may be coupled) to the insertion system 700. The insertion system 700 having the spacer 500 coupled distally thereto is advanced toward the vertebrae by aligning the insertion guide 721 with the longitudinal guide channels 209 (or longitudinal guide channels 309 when using the auxiliary blade 300). Once aligned, the channel guide 721*c* is advanced distally along the longitudinal guide channel 209 (or longitudinal guide channel 309) (block 924). Once the spacer 500 is positioned as desired by the clinician, the insertion system 700 may rotatably engage a screw engagement mechanism to remove the screw 722 from the threaded aperture 516 of the spacer 500 (block 926), though removal may not be desired or necessary, depending on the surgical procedure. The clinician places bone screws through screw bores 524 in attachment plate 520 or, in the case of expandable interbody spacer 600, through apertures 610*a*, 612*a*. It is contemplated that only one bone screw may be used with spacer 500. It is also contemplated that when using the expandable interbody spacer 600, after the expandable interbody spacer 600 is positioned between adjacent vertebrae, one bone screw is inserted through one of the apertures 610*a*, 612*a*. Subsequent to inserting the bone screw through one of the apertures 610*a*, 612*a*, the expandable interbody spacer 600 is allowed to expand and a second bone screw is inserted in the other of the apertures 610*a*, 612*a*, thereby securing the expandable interbody spacer 600 in position. Preferably, the bone screws are inserted with the plate/implant combination or the expandable interbody spacer 600, as the case may be, secured to and under the control of insertion system 700 which is tethered to the either the first or second retractor blade 200*a*, 200*b*. Attaching the plate/implant combination or the expandable interbody spacer 600 to bone while attached to and under the control of the insertion system 700, which is in turn secured relative to either the first or second retractor blade 200*a*, 200*b* which is secured to one or both of the adjacent vertebrae, assures that the position of the spacer 500 or the expandable interbody spacer 600 does not shift as the bone screws are inserted and driven into bone. In the case of insertion of expandable interbody spacer 600, the implant advantageously may be inserted into the disc space and secured to the vertebrae by bone screws with the ALL intact. It is common to release the ALL prior to inserting and securing an expandable interbody spacer 600, but releasing the ALL prior to inserting and securing the expandable interbody spacer 600 may mobilize the vertebrae and increase the likelihood that the position of the expandable interbody spacer 600 or bone screws will shift away from the desired position during insertion. Since the expandable interbody spacer 600 may be inserted in an unexpanded condition and expanded after bone screws are inserted through apertures 610*a*, 612*a* into bone to secure the expandable interbody spacer 600 relative to the vertebrae, the ALL may be released after the expandable interbody spacer 600 has been secured in place with bone screws, thereby assuring that the expandable interbody spacer 600 and/or bone screw position doesn't shift during insertion due to mobilization caused by release of the ALL. After the ALL is released with the expandable interbody spacer 600 secured in place, the expandable interbody spacer 600 may be expanded to adjust for lordosis. It is contemplated that the ALL may be released by cutting the ALL or it may be released upon expansion of the expandable interbody spacer 600.

Figure 8A:
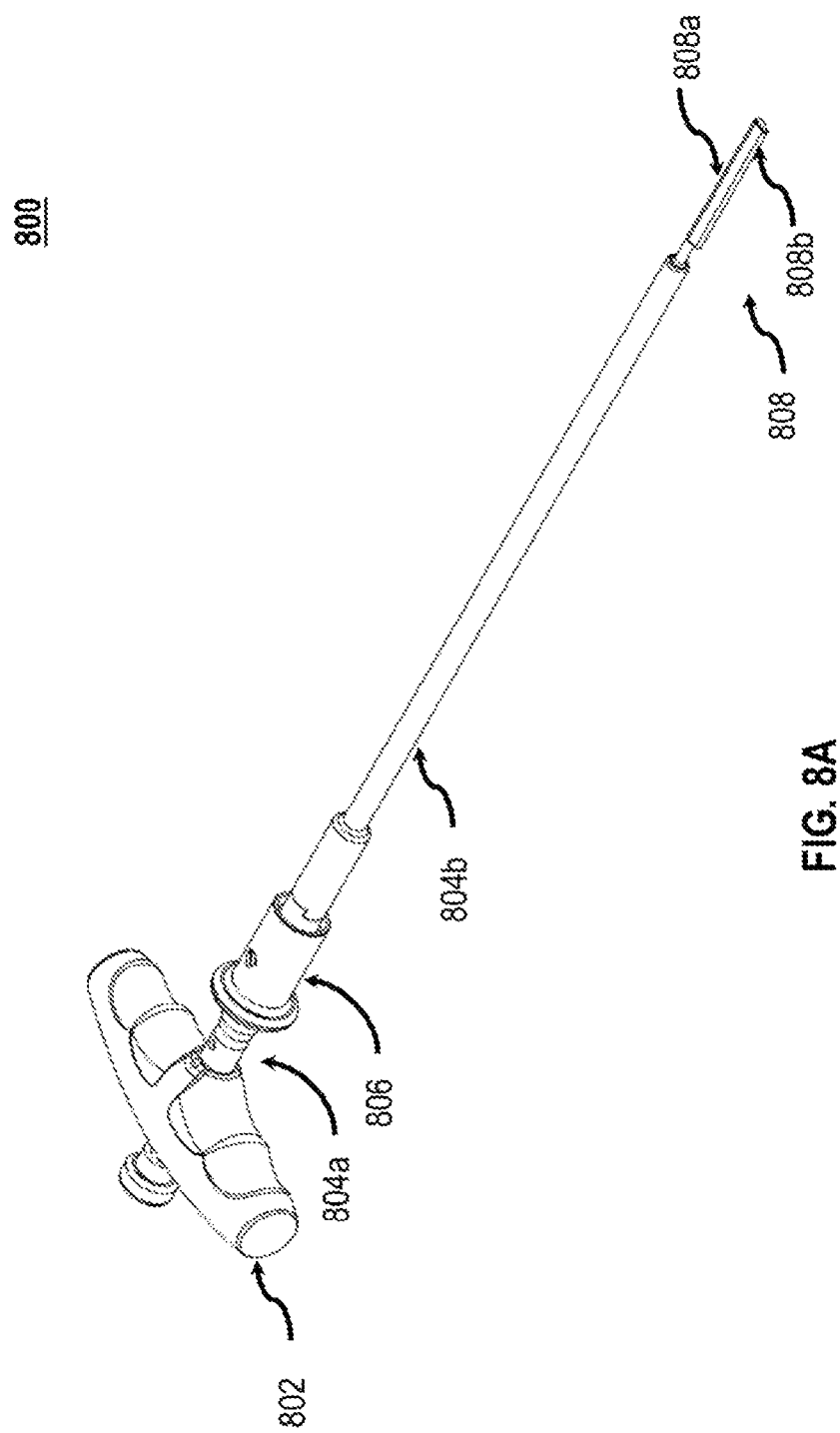
FIG. 8A is a perspective view of an expander provided in accordance with the present disclosure.

Referring now to FIG. 8A, an expander is shown for rotatably engaging and expanding an expandable interbody spacer 600 (FIGS. 5A-5G), the expander designated generally 800. The expander 800 has a handle 802, a shaft having a first section 804a and a second section 804b extending distally from the handle 802, and a blade 808 extending distally from a distal portion of the second section 804b of the shaft. The first and second sections 804a, 804b are removably coupled by a locking collar 806 coupled to the first section 804a of the shaft.

The second section 804b of the shaft has the blade 808 extending distally therefrom. The blade 808 has a rounded portion 808a and an edge 808b extending outward from the rounded portion 808a. Additionally, the blade 808 may taper from the rounded portion 808a toward the edge 808b such that the edge 808b has a thinner cross-section than the rounded portion 808a.

It will be understood that various modifications may be made to the embodiments of the presently disclosed sensing device. Specifically, while use of the insertion system 700, the insertion system 700, and the expandable interbody spacer 600 have been describe in detail in connection with the use of the retractor 100, it will be understood that the devices may be used in connection with devices known in the art. For example, the aforementioned devices may be used with known retractors or other known techniques or methods to deliver the spacer 500, or expandable interbody spacer 600, to the target site. Additionally, the spacer 500 and expandable interbody spacer 600 may be used with one or more insertion systems and/or retractors during surgical procedures. Therefore, the above description should not be construed as limiting, but merely as exemplifications of embodiments. Those skilled in the art will envision other modifications within the scope and the spirit of the present disclosure.

What is claimed is:

1. A system comprising:
   an interbody spacer having an attachment screw receiving hole;
   an inserter comprising:
      a tubular body portion;
      a rotatable screw engagement mechanism within the tubular body portion, the screw engagement mechanism including an engagement portion; and
      arms extending from a distal end of the tubular body portion; and
   a plate comprising:
      an attachment bore for receiving an attachment screw inserted therethrough to secure the plate to the interbody spacer, the plate having an axis passing through the attachment bore, wherein the engagement portion is configured to receive the attachment screw such that, when the screw engagement mechanism is rotated, the attachment screw is advanced through the attachment bore;
      one or more indents, wherein the one or more indents are configured to receive a respective arm of the inserter such that the inserter can be removably coupled directly to the plate; and
      a pair of bone screw receiving holes with a center of each bone screw receiving hole offset from a plane transverse to the axis.

2. The system of claim 1, wherein the axis is parallel to a longitudinal axis of the interbody spacer extending in a lateral to medial direction when the interbody spacer is implanted.

3. The system of claim 1, further comprising the attachment screw, wherein the attachment screw is configured to extend through the attachment bore and engage the attachment screw receiving hole to secure the plate to the interbody spacer.

4. The system of claim 1, wherein the center of each bone screw receiving hole is offset from the plane transverse to the axis on a same side of the plane.

5. The system of claim 4, wherein the center of each bone screw receiving hole is offset from the plane by an angle of from about 5 degrees to about 30 degrees.

6. The system of claim 1, wherein the interbody spacer comprises a top surface substantially parallel to a bottom surface.

7. The system of claim 1, wherein the interbody spacer comprises a first sidewall having a first height and a second sidewall having a second height different than the first height.

8. The system of claim 1, wherein the inserter is configured to mate with the interbody spacer via the attachment screw receiving hole.

9. The system of claim 1, wherein the inserter is further configured to be removably coupled to the interbody spacer.

10. The system of claim 1, wherein respective arms of the inserter further comprise respective hooks configured to be removably coupled directly to the plate.

11. A method of performing a surgical procedure, comprising:
    positioning an interbody spacer between a first vertebrae and a second vertebrae;
    releasably coupling one or more arms of an inserter to respective indents on a plate configured to be coupled to the interbody spacer, wherein the one or more arms of the inserter extend from a distal end of a tubular body portion of the inserter;
    after the interbody spacer is positioned, positioning the plate using the inserter, wherein the plate comprises a pair of bone screw receiving holes;
    coupling the plate to the interbody spacer, wherein the coupling comprises:
       receiving, by an engagement portion of a screw engagement mechanism of the inserter, an attachment screw, wherein the screw engagement mechanism is within the tubular body portion of the inserter;
       inserting an attachment screw through an attachment bore of the plate and into the attachment screw receiving hole of the interbody spacer, and
       advancing the attachment screw through the attachment bore by rotating the screw engagement mechanism;
    inserting a first bone screw into a first bone screw receiving hole of the pair of bone screw receiving holes; and
    inserting a second bone screw into a second bone screw receiving hole of the pair of bone screw receiving holes.

12. The method of 9, wherein when positioning the interbody spacer, the interbody spacer is releasably coupled to the inserter.

13. The method of 10, wherein releasably coupling the interbody spacer to the inserter comprises threadably coupling the inserter to the interbody spacer via the attachment screw receiving hole.

14. The method of claim 11, wherein releasably coupling the plate to the one or more arms of the inserter comprises releasably coupling prongs of the inserter to the respective indents of the plate.

15. The method of claim 11, wherein:
the plate comprises an axis passing through the attachment bore, and
a center of each bone screw receiving hole is offset from a plane transverse to the axis.

16. The method of claim 15, wherein the axis is parallel to a longitudinal axis of the interbody spacer extending in a lateral to medial direction when the interbody spacer is implanted.

17. The method of claim 15, wherein each bone screw receiving hole is angled such than when the first bone screw or second bone screw is inserted through the respective first and second bone screw receiving holes, the first or second bone screw is inserted into the respective first or second vertebrae.

18. A method of performing a surgical procedure, comprising:
coupling a plate to an interbody spacer, wherein:
the plate comprises an attachment bore, an axis passing through the attachment bore, and a pair of bone screw receiving holes,
the interbody spacer comprises an attachment screw receiving hole, and
the coupling comprises:
receiving, by an engagement portion of a screw engagement mechanism of an inserter, an attachment screw, wherein the screw engagement mechanism is within a tubular body portion of the inserter;
inserting the attachment screw through the attachment bore into the attachment screw receiving hole; and
advancing, by rotating the screw engagement mechanism, the attachment screw into the attachment screw receiving hole;
after coupling the plate to the interbody spacer, releasably coupling one or more arms of the inserter to respective indents on the plate;
after releasably coupling the one or more arms of the inserter to the respective indents on the plate, positioning the coupled plate and interbody spacer between a first vertebrae and a second vertebrae;
inserting a first bone screw into a first bone screw receiving hole of the pair of bone screw receiving holes; and
inserting a second bone screw into a second bone screw receiving hole of the pair of bone screw receiving holes.

19. The method of claim 18, wherein releasably coupling one or more arms of the inserter to the plate comprises releasably coupling prongs of the inserter to the respective indents of the plate.

20. The method of claim 18, wherein:
a center of each bone screw receiving hole is offset from a plane transverse to the axis, and
the axis is parallel to a longitudinal axis of the interbody spacer extending in a lateral to medial direction when the interbody spacer is implanted.

* * * * *